United States Patent
Arenberg et al.

(10) Patent No.: US 8,197,461 B1
(45) Date of Patent: Jun. 12, 2012

(54) CONTROLLED RELEASE SYSTEM FOR DELIVERING THERAPEUTIC AGENTS INTO THE INNER EAR

(75) Inventors: Irving K. Arenberg, Englewood, CO (US); Michael H. Arenberg, Englewood, CO (US); Christine Lemke, Denver, CO (US); John A. Berglund, Lafayette, CO (US)

(73) Assignee: Durect Corporation, Cupertino, CA (US)

( * ) Notice: Subject to any disclaimer, the term of this patent is extended or adjusted under 35 U.S.C. 154(b) by 0 days.

(21) Appl. No.: 09/205,251

(22) Filed: Dec. 4, 1998

(51) Int. Cl.
*A61M 31/00* (2006.01)
(52) U.S. Cl. .................................................. 604/500
(58) Field of Classification Search .............. 604/1–2, 604/11–18, 57–64, 500, 514, 506, 890.1, 604/891.1, 892.1, 904; 606/108–109; 128/898; 424/422, 423–426, 437
See application file for complete search history.

(56) References Cited

U.S. PATENT DOCUMENTS

| | | | |
|---|---|---|---|
| 2,642,065 A | 6/1953 | Negri | |
| 3,528,419 A | 9/1970 | Joechle et al. | |
| 3,982,545 A | 9/1976 | Silverstein | |
| 4,034,759 A | 7/1977 | Haerr | |
| 4,141,973 A | 2/1979 | Balazs | |
| 4,159,719 A | 7/1979 | Haerr | |
| 4,226,848 A | 10/1980 | Nagai et al. | |
| 4,297,748 A | 11/1981 | Moloy | |
| 4,343,931 A | 8/1982 | Barrows | |
| 4,472,394 A * | 9/1984 | Peterson | 514/179 |
| 4,784,640 A * | 11/1988 | Johnson et al. | |
| 4,851,402 A * | 7/1989 | Jacobs et al. | |
| 4,874,368 A | 10/1989 | Miller et al. | |
| 5,236,413 A | 8/1993 | Feiring | |
| 5,304,134 A | 4/1994 | Kraus et al. | |
| 5,344,411 A | 9/1994 | Domb et al. | |
| 5,350,580 A | 9/1994 | Muchow et al. | |
| 5,419,312 A | 5/1995 | Arenberg et al. | |
| 5,421,818 A | 6/1995 | Arenberg | |
| 5,437,656 A | 8/1995 | Shikani et al. | |
| 5,442,053 A | 8/1995 | della Valle et al. | |
| 5,461,140 A | 10/1995 | Heller et al. | |
| 5,474,529 A | 12/1995 | Arenberg | |
| 5,476,446 A | 12/1995 | Arenberg | |
| 5,512,055 A | 4/1996 | Domb et al. | |

(Continued)

FOREIGN PATENT DOCUMENTS

DE 195 09 029 9/1996
(Continued)

OTHER PUBLICATIONS

Arriaga, M., et. al. "Hearing Results of Intratympanic Steroid Treatment of Endolymphatic Hydrops", *Laryngoscope*, 108:1682-1685 (Nov. 1998).

(Continued)

*Primary Examiner* — Theodore Stigell

(57) ABSTRACT

A specialized drug delivery unit for inner ear treatment which employs a portion of carrier media material containing one or more therapeutic agents therein. The carrier media material is designed to release the therapeutic agents in a controlled manner over time. The drug delivery unit is sized for placement in the round window niche of a patient. The released therapeutic agents come in contact with the round window membrane and pass therethrough into the inner ear for treatment purposes. This system provides many benefits ranging from the ability to deliver drugs in a site specific, highly controlled manner to the transfer of such materials with minimal patient discomfort and monitoring requirements.

26 Claims, 4 Drawing Sheets

U.S. PATENT DOCUMENTS

| | | | |
|---|---|---|---|
| 5,572,594 | A | 11/1996 | Devoe et al. |
| 5,695,458 | A | 12/1997 | Shikani et al. |
| 5,736,524 | A | 4/1998 | Content et al. |
| 5,954,682 | A | 9/1999 | Petrus |
| 6,045,528 | A | 4/2000 | Arenberg et al. |
| 6,177,434 | B1 * | 1/2001 | Kopke et al. |
| 6,228,371 | B1 | 5/2001 | Nano |
| 6,239,116 | B1 | 5/2001 | Krieg et al. |
| 6,685,697 | B1 | 2/2004 | Arenberg et al. |
| 2004/0186098 | A1 * | 9/2004 | Magal .................. 514/217.12 |

FOREIGN PATENT DOCUMENTS

| | | |
|---|---|---|
| WO | WO97/38698 | 10/1997 |
| WO | WO 97/38698 | * 10/1997 |
| WO | WO 9738698 A1 | * 10/1997 |
| WO | 0004854 | 3/2000 |

OTHER PUBLICATIONS

Balough, B., et al., "Kinetics of gentamicin uptake in the inner ear of *Chinchilla langier* after middle-ear administration in a sustained-release vehicle" *Otolaryngol. Head Neck Surg.*, 119(5)427-431 (Nov. 1998).

Finne, U., et al., "Timolol release from matrices of monoesters of poly (vinyl methyl ether-maleic anhydride): effects of polymer molecular weight and a basic additive", *J. Pharmaceutical Science*, 80(7):670-673 (1991).

Golomb, G., et al., "Controlled-Release Drug Delivery of Diphosphonates to Inhibit Bioprosthetic Heart Valve Calcification: Release Rate Modulation with Silicone Matrices via Drug Solubility and Membrane Coating", *J. Pharm. Sci.*, 76(4):271-276 (1987).

Goycoolea, M., et al., "Extended Middle Ear Drug Delivery", *Acta Otolaryngol. (Stockh.)*, Suppl. 493:119-126 (1992).

Goycoolea, M., et al., "In Search of Missing Links in Otology, II. Development of an Implantable Middle Ear Drug Delivery System: Initial Studies of Sustained Ampicillin Release for the Treatment of Otitis Media", *Laryngoscope*, 101:727-732 (Jul. 1991).

Hamalainen, K., et al., "Roles of acid/base nature and molecular weight in drug release from matrices of gelfoam and monoisopropyl ester of poly (vinyl methyl ether-maleic anhydride)", *Journal of Controlled Release*, 56:273-283 (1998).

Hollinger, J. (Ed.), "Biomedical Applications of Synthetic Biodegradable Polymers", CRC Press, Boca Raton, FL (USA), Ch. 4 by Laurencin, C., pp. 59-102 (1995).

Husmann, K., et al., "Round Window administration of gentamicin: a new method for the study of ototoxicity of cochlear hair cells", *Hearing Research*, 125:109-119 (1998).

Langer, R., "Drug delivery and targeting", *Nature*, vol. 392/Supp, pp. 5-10 (Apr. 30, 1998)

Leong, K., et al., "Bioerodable polyanhydrides as drug-carrier matrices: I. Characterization, degradation, and release characteristics", *J. Biomedical Materials Research*, 19(8):941-955 (1985).

Liening, D., et al., "A Comparison of the biocompatibility of three absorbable hemostatic agents in the rat middle ear", *Otolaryngol. Head Neck Surg.*, 116(4):454-457 (1997).

Lundsman, L., et al., "Premeability of the Normal Round Window Membrane to *Haemophilus influenzae* Type b Endotoxin", *Acta Otolaryngol. (Stockh.)*, 112(3)524-529 (1992).

Park, M., et al., "Sustained Release of Antibiotic From a Fibrin-Gelatin-Antibiotic Mixture", *Laryngoscope*, 107:1378-1381 (Oct. 1997).

Portmann, M., "Electrophysiological correlates of endolymphatic hypertension and endolymphatic hydrops: an overview of electrocochleography (ECoG)", Proceedings of the Third International Symposium and Workshops on the Surgery of the Inner Ear, Snowmass, CO (USA) Jul. 29-Aug. 4, 1990 as reported in *Inner Ear Surgery*, edited by I. Kaufman Arenberg, Kugler Publications, Amsterdam/New York, pp. 241-247 (1991).

Ramsay, H., et al., "A Simple Technique for Introducing Anterograde and Retrograde Tracers into the Vestibular and Cochlear Sensory Organs", *Acta Otolarvngol. (Stockh.)*, 116(1):39-43 (1996).

Ruan, R., et al., "Ototoxicity of sodium nitroprusside", *Hearing Research*, 114:169-178 (1997).

Silverstein, H., et al., "Intratympanic Steroid Treatment of Inner Ear Disease and Tinnitus (Preliminary Report) ", *ENT—Ear, Nose, and Throat Journal*, 75-(8):468-488 (Aug. 1996).

Silverstein, H., "Streptomycin Treatment for Meniere's Disease", *Annals of Otology, Rhinology & Laryngology—Supplement*, 112:44-48 (1984).

Wanamaker, H., et al., "Dose-Related Vestibular and Cochlear Effects of Transtympanic Gentamicin", *The American Journal of Otology*, 19:170-179 (1998).

Data Sheets involving Gelfoam® brand of absorbable gelatin sterile powder (absorbable gelatin powder from absorbable gelatin sponge, USP) from Phamacia & Upjohn, Kalamazoo, MI (USA), (Jul. 1996).

Data Sheets involving Gelfoam® brand of absorbable gelatin dental packs (absorbable gelatin sponge, USP) from Pharmacia & Upjohn, Kalamazoo, MI (USA), (Mar. 1993).

Data Sheets involving Gelfoam® brand of absorbable gelatin sponge, USP from Pharmacia & Upjohn, Kalamazoo, MI (USA), (Sep. 1998).

Pending U.S. Appl. No. 08/874,208, filed Jun. 13, 1997 to Arenberg et al.

Pending U.S. Appl. No. 09/121,460, filed Jul. 23, 1998 to Arenberg et al.

Merkli, A., et al., "Characterization of a new biodegradable semi-solid poly (orthoester) for drug delivery systems", *Journal of Biomaterial Sciences*, Polymer Edition, 4:505-516 (1993).

Tamada, J., et al., "The development of polyanhydrides for drug delivery applications", *Journal of Biomaterial Sciences*, Polymer Edition, 3(4) :315-353 (1992).

Hellstrom, et al., (Sep.-Oct. 1983) "Absorbable Gelatin Sponge (Gelfoam) in Otosurgery: One Cause of Undesirable Postoperative Results?" *Acta Otolaryngol (Stockh)* vol. 96(3-4):269-75.

Laurent, et al., (May-Jun. 1986) "Hyaluronic Acid Reduces Connective Tissue Formation in Middle Ears Filled with Absorbable Gelatin Sponge: an Experimental Study," *Am J Ontolaryngol* vol. 7(3):181-6.

Liening, et al., (1997) "A Comparison of the Biocompatibility of Three Absorbable Hemostatic Agents in the Rat Middle Ear," *Otolaryngol Head Neck Surg* vol. 116:454-457.

Lundman, et al. (1992) "Permeability of the Normal Round Window Membrane to *Haemophilus influenzae* Type b Endotoxin," *Acta Otolaryngol (Stockh)* vol. 112:524-529.

Shea, et al., (Jul. 16-23, 1994) "Streptomycin Perfusion of the Labyrinth Through the Round Window Plus Intravenous Streptomycin for Benign Paroxysmal Positional Vertigo," 4th International Symposium and Workshops . . . Inner Ear medicine and Surgery Prosper Meniere Society: Snowmass-Aspen, Colorado.

Shea, (1997) "The Role of Dexamethasone or Streptomycin Perfusion in the Treatment of Meniere's Disease," *Otolaryngol. Clin. North Amer.* vol. 30(6):1051-9.

Shea, et al., (1996) "Dexamethasone Perfusion of the Labyrinth Plus Intravenous Dexamethasone for Meniere's Disease," *Otolaryngol. Clin. North Amer.* vol. 29(21:353-358.

Silverstein, et al., (1998) "Dexamethasone Inner Ear Perfusion for the Treatment of Menier's Disease: A Prospective, Randomized, Double-Blind, Crossover Trial," *The American journal of Otology* vol. 19:196-201.

Silverstein, et al., (1997) "Inner Ear Perfusion and the Role of Round Window Patency," *Am J Otol* vol. 18(5):586-9.

* cited by examiner

CONTROLLED RELEASE SYSTEM FOR DELIVERING THERAPEUTIC AGENTS INTO THE INNER EAR

BACKGROUND OF THE INVENTION

The present invention generally relates to a method for therapeutically treating the inner ear. More particularly, the invention involves a specialized, minimally-invasive technique for transporting therapeutic agents (e.g. drugs and other pharmaceutical compositions) into the inner ear from the middle ear in a highly effective manner.

In order to treat ear disorders, it may often be necessary to deliver therapeutic agents to various ear tissues in a controlled, safe, and efficient manner. For example, a variety of structures have been developed which are capable of delivering/administering therapeutic agents into the external auditory canal of the outer ear. U.S. Pat. No. 4,034,759 to Haerr discloses a hollow, cylindrical tube manufactured of sponge material (e.g. dehydrated cellulose) which is inserted into the external auditory canal of a patient. When liquid medicines are placed in contact with the tube, it correspondingly expands against the walls of the auditory canal. As a result, accidental removal of the tube is prevented. Furthermore, medicine materials absorbed by the tube are maintained in contact with the walls of the external auditory canal for treatment purposes. Other absorbent devices designed for treatment of the external auditory canal and related tissue structures are disclosed in U.S. Pat. No. 3,528,419 to Joechle, U.S. Pat. No. 4,159,719 to Haerr, and U.S. Pat. No. 2,642,065 to Negri. The Negri patent specifically describes a medicine delivery device with an internally-mounted, frangible medicine container which, when broken, releases liquid medicines into an absorbent member.

However, the delivery of therapeutic agents in a controlled and effective manner is considerably more difficult with respect to tissue structures of the inner ear (e.g. those portions of the ear surrounded by the otic capsule bone and contained within the temporal bone which is the most dense bone tissue in the entire human body). The same situation exists in connection with tissue materials which lead into the inner ear (e.g. the round window membrane). Exemplary inner ear tissue structures of primary importance for treatment purposes include but are not limited to the cochlea, the endolymphatic sac/duct, the vestibular labyrinth, and all of the compartments (and connecting tubes) which include these components. Access to these and other inner ear tissue regions is typically achieved through a variety of structures, including but not limited to the round window membrane, the oval window/stapes footplate, the annular ligament, and the otic capsule/temporal bone, all of which shall be considered "middle-inner ear interface tissue structures" as described in greater detail below. Furthermore, as indicated herein, the middle ear shall be defined as the physiological air-containing tissue zone behind the tympanic membrane (e.g. the ear drum) and ahead of the inner ear.

The inner ear tissues listed above are of minimal size and only readily accessible through invasive microsurgical procedures. In order to treat various diseases and conditions associated with inner ear tissues, the delivery of medicines to such structures is often of primary importance. Representative medicines which are typically used to treat inner ear tissues include but are not limited to urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin), antioxidants, neurotrophins, nerve growth factors, various therapeutic peptides, and polysaccharides. Of particular interest in this list are compounds which are used to alter the permeability of the round window membrane within the ear using, for example, hyaluronidase and iontophoretic techniques (defined below). Likewise, the treatment of inner ear tissues and/or fluid cavities may involve altering the pressure, volume, electrical activity, and temperature characteristics thereof. Specifically, a precise balance must be maintained with respect to the pressure of various fluids within the inner ear and its associated compartments. Imbalances in the pressure and volume levels of such fluids can cause various problems, including but not limited to conditions known as endolymphatic hydrops, endolymphatic hypertension, perilymphatic hypertension, perilymphatic hydrops, perilymphatic fistula, intracochlear fistula, Meniere's disease, tinnitus, vertigo, hearing loss related to hair cell or ganglion cell damage/malfunction, and ruptures in various membrane structures within the ear.

Of further interest regarding the delivery of therapeutic agents to the middle ear, inner ear, and middle-inner ear interface tissue structures are a series of related and co-owned patents, namely, U.S. Pat. Nos. 5,421,818; 5,474,529, and 5,476,446 all to Arenberg et al. which are likewise all incorporated herein by reference. Each of these patents discloses a medical treatment apparatus designed to deliver fluid materials to internal ear structures. U.S. Pat. No. 5,421,818 describes a treatment system which includes a tubular stem attached to a reservoir portion with an internal cavity designed to retain a supply of therapeutic fluid compositions therein. The side wall of the reservoir portion further comprises fluid transfer means (e.g. pores, a semi-permeable membrane, and the like). Contact between the fluid transfer means and the round window membrane in a patient allows fluid materials to be delivered on-demand to the round window membrane, followed by diffusion of the fluid materials through the membrane into the inner ear. U.S. Pat. No. 5,474,529 involves a therapeutic treatment apparatus with a plurality of reservoir portions (e.g. a first and a second reservoir portion in a preferred embodiment) which are connected to multiple tubular stems that are designed for implantation into, for example, the endolymphatic sac and duct using standard microsurgical techniques. Finally, U.S. Pat. No. 5,476,446 discloses a therapeutic treatment apparatus which includes a reservoir portion for retaining liquid medicine materials therein, a first tubular stem on one side of the reservoir portion, and a second tubular stem on the opposite side of the reservoir portion. The second stem is designed to reside within the external auditory canal of a patient lateral to the ear drum, while the first stem is sized for placement within an opening formed in the stapes footplate/annular ligament so that medicine materials in fluid form can be delivered into the inner ear from the reservoir portion (which resides in the middle ear cavity medial to the ear drum).

A different approach for transferring materials into and out of the inner ear via the round window niche/round window membrane is disclosed in co-owned pending U.S. patent application Ser. No. 08/874,208 (Arenberg et al.) entitled "INNER EAR FLUID TRANSFER AND DIAGNOSTIC SYSTEM" and filed on Jun. 13, 1997 which is incorporated herein by reference. This application describes a system in which one or more fluid transfer conduits are provided which are operatively connected to a "cover member" that is designed for placement on top of the niche (e.g. at its point of entry) or within the niche. The cover member is used to create a "fluid-receiving zone" (or "inner ear fluid transfer space") which is partially or entirely sealed in order to facilitate fluid transfer into and out of the inner ear. In one embodiment, the cover member consists of a thin, solid, plate-like structure that is secured in position on top of the niche at its point of entry as previously noted. Alternatively, the cover member may comprise a portion of flexible and compressible material which, during placement within the round window niche, is compressed and thereafter allowed to expand once the portion of compressible material is positioned within the niche. As a result, the cover member can engage the internal side wall of the round window niche, thereby creating the fluid-receiving zone ("inner ear fluid transfer space") between the compressible cover member and the round window membrane. Representative compositions used to construct the portion of compressible material associated with the cover member in this particular embodiment optimally involve foam-type products including but not limited to polyethylene foam, polyether foam, polyester foam, polyvinyl chloride foam, polyurethane foam, and sponge rubber (e.g. synthetic or natural), all of which are of the closed cell variety. Such materials are non-fluid-absorbent in accordance with the substantial lack of open cells therein. Specifically, the non-fluid-absorbent character of these materials results from the closed cell structure thereof which prevents fluid materials from being absorbed compared with open cell (absorbent) foam products.

A still further system for transferring materials into and out of the inner ear via the round window niche/round window membrane is disclosed in co-owned pending U.S. patent application Ser. No. 09/121,460 (Arenberg et al.) entitled "FLUID TRANSFER AND DIAGNOSTIC SYSTEM FOR TREATING THE INNER EAR" and filed on Jul. 23, 1998 which is also incorporated herein by reference. This particular system employs a fluid transfer conduit which includes one or more passageways therethrough. The fluid transfer conduit may also have a semipermeable membrane associated therewith to control fluid flow. Attached to the conduit is an inflatable bladder sized for insertion within the round window niche. When inflated, the bladder engages the internal side wall of the niche, thereby securing the bladder and part of the conduit within the niche. The conduit can then transfer fluids to and from the niche and the fluid-permeable round window membrane therein. Bladder inflation may be achieved through one of the passageways within the conduit which can deliver an inflation fluid into the bladder. Also, the conduit may include an elongate conductive diagnostic member for transferring electrical potentials to and from the inner ear (via the round window membrane).

Notwithstanding the approaches described above which provide a number of benefits, the present invention involves an improved minimally-invasive drug delivery system and method which offers many additional advantages including: (1) the repeatable and sustained active/passive delivery of therapeutic agents into the inner ear through the round window membrane (or other middle-inner ear interface structures as discussed further below); (2) the delivery of a wide variety of therapeutic agents (e.g. pharmaceutical preparations) in a safe and direct manner through the use of controlled-release carrier materials; (3) the accomplishment of effective drug delivery without overly invasive surgical procedures; (4) the ability to initiate a single drug delivery step which will result in the controlled/sustained delivery of therapeutic agents into the inner ear of a patient without further medical procedures, monitoring, and patient discomfort; and (5) achievement of the benefits described above through the use of a controlled release carrier media material which is combined with one or more therapeutic agents (e.g. pharmaceutical compositions) and placed into the round window niche of a patient in the form of a mass consisting of a pellet or other structural unit. In addition, as outlined further below, the carrier medial material and therapeutic agent(s) can be placed into the round window niche in the form of a gel/paste that is initially injected into the niche to form the mass in situ. The mass of material associated with the carrier media composition (which is positioned adjacent to or directly against the round window membrane) subsequently releases the therapeutic agents over time. As a result, the therapeutic agents travel through the round window niche, followed by movement into and through the round window membrane. The therapeutic agents thereafter enter the inner ear for treatment purposes. This passive, minimally-invasive drug delivery system allows pharmaceutical compositions to be effectively delivered into the inner ear of a patient in a controlled and efficient fashion. In this manner, a highly accurate transfer system for therapeutic agents is created. Accordingly, the present invention represents an advance in the art of inner ear treatment, diagnosis, and medicine delivery as described in detail below.

SUMMARY OF THE INVENTION

It is an object of the present invention to provide a system for delivering therapeutic agents to inner ear tissues and tissue regions in a highly effective manner.

It is another object of the invention to provide a system for delivering therapeutic agents to inner ear tissues and tissue regions which is accomplished with a minimal degree of surgical intervention.

It is another object of the invention to provide a system for delivering therapeutic agents to inner ear tissues and tissue regions which is capable of controlled and sustained (e.g. time-release) drug transfer in an accurate and selective manner.

It is another object of the invention to provide a system for delivering therapeutic agents to inner ear tissues and tissue regions which is capable of being used effectively in patients of all ages and is likewise able to deliver a wide variety of therapeutic agents in differing dosages. These dosages include microdosing situations where drugs are to be supplied in nanogram or microgram quantities.

It is a still further object of the invention to provide a system for delivering therapeutic agents to inner ear tissues and tissue regions which is accomplished with a minimal degree of patient discomfort.

It is a still further object of the invention to provide a system for delivering therapeutic agents to inner ear tissues and tissue regions that is safe, effective, and requires little if any physician monitoring.

It is an even further object of the invention to provide a system for delivering therapeutic agents to inner ear tissues and tissue regions which involves a minimal level of expense and can be used to treat a wide variety of inner ear conditions.

It is an even further object of the invention to provide a system for delivering therapeutic agents to inner ear tissues and tissue regions which provides the treating physician with a considerable degree of control over the duration of drug delivery, the rate of drug transfer into the inner ear, and the types of drugs which may be administered.

It is an even further object of the invention to provide a system for delivering therapeutic agents to inner ear tissues and tissue regions wherein the benefits listed above are achieved through the use of a controlled release carrier media material which is combined (e.g. impregnated or coated with) one or more therapeutic agents. The carrier media material (in the form of a discrete unit or "mass") is then inserted directly into the round window niche of a patient adjacent to or against the round window membrane. The natural physiological environment of the round window niche (including the pH, temperature level, and moisture level thereof) cooperates with the carrier media material to cause the drug materials to be released therefrom. As this step occurs, the carrier media material (if biodegradable in a preferred embodiment) is absorbed into adjacent tissue regions and thereafter metabolized by the body. When other, non-biodegradable compositions are employed for carrier media purposes (which, for example, chemically break-down over time), they may be physically removed from the round window niche after drug delivery.

After release of the therapeutic agent into the round window niche as discussed above, it passes into and through the round window membrane. This step is accomplished in accordance with a variety of physical interactions between the therapeutic agent and the round window membrane including the following processes: osmosis, diffusion, active/passive transport, or a combination thereof. There are other important details, modifications, and embodiments associated with this unique process which will be discussed further below. As a result, the desired therapeutic agents (e.g. drug compounds) are delivered in a controlled, complete, substantially automatic, and uniform manner with a minimal degree of patient discomfort and physician interaction. In this regard, the present invention represents a substantial advance in the treatment of inner ear tissues and otologic drug delivery.

As noted above, the present invention involves a highly effective and minimally-invasive method for the controlled and site-specific transfer (e.g. "microdosing") of physician-specified therapeutic agents into the inner ear via the round window membrane (which is centrally located within the round window niche as previously discussed). While the invention shall primarily be described herein with reference to the round window membrane/round window niche, it shall also be applicable to other internal cavities within the ear which will become readily apparent from the discussion provided below. Thus, all of the information presented herein regarding the claimed materials, methods, and their relationship to the round window niche shall be incorporated by reference relative to other internal ear cavities (natural or man-made) without limitation.

The following summary of the present invention represents a general overview of the novel features mentioned above. A more detailed, specific, and enabling disclosure of the invention will be presented later in the Detailed Description of Preferred Embodiments. To accomplish the goals recited herein, a discrete drug delivery unit is first provided. The drug delivery unit (which is sized for partial or complete placement within the round window niche or other internal ear cavity as previously noted) is comprised of two main components, namely, (1) a mass of at least one controlled release carrier media material; and (2) one or more selected therapeutic agents combined (preferably but not exclusively in a homogeneous manner) with the carrier medial material. The term "therapeutic agents" shall be construed to encompass drugs and any other materials in liquid, solid, semi-solid, crystalline, or other forms which provide therapeutic benefits in connection with inner ear tissues or the other tissues of interest. Supplemental compositions including but not limited to plasticizers, lubricants, and the like may also be employed within the drug delivery unit in selectively-variable amounts as needed and determined by preliminary pilot testing. In this regard, the present invention shall not be restricted to any particular carrier media materials, therapeutic agents, supplemental compositions, quantities of these ingredients, and other operational parameters unless otherwise specified herein. Representative materials which may be employed in connection with the ingredients used to produce the claimed drug delivery units shall be listed below in the Detailed Description of Preferred Embodiments section. However, it is important to note that the carrier media material should be of synthetic origin (without any animal-derived products combined therewith) in order to avoid allergic reactions, biological rejection, and other adverse effects which may be caused by animal-derived products (including but not limited to gelatin materials, collagen products, and the like). In this regard, the term "synthetic" as used herein shall be defined to encompass compositions of a non-animal origin as discussed further below, with the placement of a synthetic carrier media material directly in the round window niche constituting a novel development with a high safety profile. It should also be noted that the term "animal" as used herein shall also encompass humans. Thus, the word "synthetic" shall likewise exclude products of human origin.

The selected drug delivery unit (which may be configured in many different forms without limitation including pellets, disks, spheres, cubes, cylindrical units, strands, amorphous masses, gels, pastes, and the like) is then placed within the round window niche of the subject under consideration. The term "placement" or "placed" as used herein shall involve either partial or complete insertion of the drug delivery unit into the round window niche or other ear cavity of interest (e.g. as much as is needed in accordance with the medical procedure[s] of interest). Since a preferred embodiment of the invention will involve placement of the drug delivery unit in the round window niche, the remainder of this discussion will again focus on this location with the understanding that it is equally applicable to insertion of the drug delivery unit in other ear cavities as previously noted.

As outlined in greater detail below, the round window niche includes an internal side wall therein. Immediately upon placement of the drug delivery unit within the round window niche, it will come in direct physical contact with the internal side wall of the niche. Likewise, in view of the relatively small size of the niche, insertion of the drug delivery unit therein will typically cause it to be located directly adjacent to or against the round window membrane. However, it shall be noted that the claimed method is highly effective regardless of the particular orientation of the drug delivery unit relative to the round window membrane. Once the drug delivery unit is positioned (e.g. placed) within the round window niche as discussed above, the carrier media material will dissolve, swell, or otherwise undergo physical changes. As a result of these changes the drug delivery unit is allowed to release the desired therapeutic agents in accordance with the mechanisms discussed herein. The term "allowed" as used in connection with the release of therapeutic agents from the drug delivery unit shall involve leaving the drug delivery unit in the patient until therapeutic agent release occurs on a partial or complete basis. This may involve a time period ranging from minutes to hours depending on the compositions under consideration. The precise physical mechanism associated with drug release will depend on the particular carrier media material being used as discussed below. Therapeutic agent release is accomplished over time in accordance with the unique physical environment of the round window niche including its pH, temperature, moisture characteristics, the type of carrier medial material being employed, and other comparable factors. If the carrier media material associated with the drug delivery unit is biodegradable, it will ultimately be absorbed into adjacent tissues in the body, followed by metabolic degradation thereof. Non-biodegradable materials may be removed by the treating physician after drug delivery using a number of minimally-invasive surgical techniques.

During the foregoing process, the previously-entrained therapeutic agent will be released from the drug delivery unit and will thereafter come in contact with the round window membrane. The therapeutic agent will then pass through the membrane in accordance with a variety of natural physical processes including but not limited to osmosis, diffusion, active/passive transport, or a combination thereof. The therapeutic agents can then effectively treat the inner ear tissues of concern.

The time needed to achieve complete release of the therapeutic agent from will vary in view of numerous factors including but not limited to the type of carrier media material being employed, the overall size of the drug delivery unit, the ambient environmental conditions with the round window niche, and other considerations as determined by routine preliminary investigation. Delivery times can range from a few hours to many months which may be adjusted in accordance with the factors listed above. In this regard, the claimed invention shall not be restricted to any drug delivery times or materials associated with the drug delivery unit as previously indicated. Likewise, specific examples of these items will again be presented below in the Detailed Description of Preferred Embodiments section.

The process described herein again offers a number of important benefits. In particular, site-specific transfer of the desired therapeutic agents into the inner ear can occur in a controlled, complete, and uniform manner with minimal patient discomfort. Likewise, as previously discussed, the claimed process is characterized by a high level of versatility in connection with (1) the size of the drug delivery units being employed; (2) the particular therapeutic agents combined with the carrier media material; and (3) the specific ingredient proportions within the drug delivery units including the concentrations of therapeutic agents (which can be varied as needed). In accordance with these benefits, the present invention represents a significant advance in inner ear therapy which enables treatment to occur in a very efficient, substantially automatic manner with minimal monitoring requirements.

As a further note, drug delivery time may be modified (e.g. increased or decreased) in connection with a given drug delivery unit through the addition of supplemental fluid materials (including but not limited to water, saline solution, and the like). The need for supplemental fluid addition will be determined in accordance with routine preliminary testing on the patient and drug delivery units under consideration. Furthermore, supplemental fluid transfer to the selected drug delivery unit within the round window niche (or other internal ear cavity) may be accomplished using the particular devices disclosed in co-owned U.S. Pat. Nos. 5,421,818; 5,474,529, and 5,476,446 all to Arenberg et al., as well as co-owned pending U.S. patent application Ser. Nos. 08/874,208 (filed on Jun. 13, 1997) and 09/121,460 (filed on Jul. 23, 1998) which are also to Arenberg et al. The quantity of supplemental fluid materials to be delivered will depend on many factors as determined by initial patient testing including but not limited to the carrier media material being employed, the desired drug delivery rate, and the like.

In an alternative embodiment to be discussed in further detail below, the drug delivery units of the present invention may be adhered to or formed on the terminal end of an elongate member. The end of the elongate member having the drug delivery unit thereon is then inserted into the round window niche as discussed above. This technique substantially facilitates insertion and subsequent physical manipulation of the drug delivery unit within the round window niche. The elongate member may remain attached to the drug delivery unit during release of the therapeutic agent or can be configured to detach from the drug delivery unit after placement thereof in the round window niche. On-demand detachment can be accomplished by selection of the manner in which the drug delivery unit is secured to the elongate member (for example, by choosing the proper adhesive, etc.)

The present invention shall not be restricted to any particular elongate members or size parameters associated with these structures which may be varied as needed. The elongate members may involve solid rod or strip-like units, hollow members of tubular configuration, and the like. A hollow, tubular elongate member is of considerable value in facilitating the flow of supplemental fluid materials to the drug delivery unit as noted above (if such fluid materials are to be employed). The elongate members may be produced from many different materials including but not limited to plastics (e.g. polyethylene or polycarbonate materials suitable for medical use).

In a still further embodiment, the drug delivery unit may be formed on the terminal end of an elongate member made of an electrically conductive material (e.g. metal) which is optimally configured in the form of a wire as disclosed in U.S. Pat. Nos. 5,421,818; 5,474,529, and 5,476,446 all to Arenberg et al. The terminal end of this structure (with the drug delivery unit adhered thereto or molded thereon) can then be inserted into the round window niche, with drug delivery occurring as discussed above.

The elongate member made of conductive material (also characterized herein as an "elongate conductive member") constitutes an electrical potential transmission system which is used to transmit electrical potentials into and out of the inner ear, preferably through the round window membrane. The term "potential" shall be broadly construed to encompass any type of electrical signal, current, voltage, or impulse regardless of form, magnitude, or origin. In a preferred embodiment discussed in substantial detail below, the elongate conductive member will involve a metallic wire, strip, or other comparable structure with a ball, loop, mushroom, flat, or spoon-shaped tip on the terminal end which preferably protrudes in an outward direction from the drug delivery unit. By placing the tip in direct physical contact with the round window membrane during use of the claimed apparatus (or in contact with tissue materials adjacent thereto which shall be deemed equivalent, namely, the mucosa/bone of the round window niche and others), a number of important steps will then take place. These steps include: (1) dissolution or chemical break-down of the carrier media material used to produce the drug delivery unit, followed by drug transfer into and through the round window membrane; and (2) the transmission of evoked or non-evoked electrical potentials to and/or from the membrane for therapeutic analysis and other purposes using various techniques preferably encompassed within the term "electrocochleography" or "ECoG". Iontophoresis procedures may also be facilitated using the components listed above, with this term being defined to involve a process in which electrical energy is employed to alter the permeability characteristics of the round window membrane. Iontophoresis can be used to facilitate transfer of the released drug materials into and through the round window membrane.

As noted above, the selection of any given procedure for placing the drug delivery unit into the round window niche (or other designated internal ear cavity) will again be determined in accordance with preliminary pilot testing involving the patient under consideration, the conditions being treated, the materials being employed in connection with the drug delivery unit and other related factors. The present invention shall therefore not be restricted to any given approach for placing the drug delivery unit into the round window niche of a patient.

The present invention represents an advance in the art of inner ear therapy and treatment. The claimed treatment system provides numerous benefits and capabilities as previously noted including but not limited to: (1) the repeatable and sustained delivery of therapeutic agents into the inner ear via the round window membrane (or other middle-inner ear interface tissue structures; (2) the delivery of many different therapeutic agents (e.g. pharmaceutical preparations) to the inner ear in a safe and direct manner; (3) the accomplishment of effective drug delivery without overly invasive surgical procedures; and (4) the use of a single-step method to deliver therapeutic agents into the inner ear of a patient without complex medical procedures, monitoring, and patient discomfort. For these reasons and the other reasons listed below, the claimed invention represents a substantial advance in the art of otological treatment and drug delivery.

These and other objects, features, and advantages of the invention will become readily apparent from the following Brief Description of the Drawings and Detailed Description of Preferred Embodiments.

DETAILED DESCRIPTION OF PREFERRED EMBODIMENTS

Figure 1:
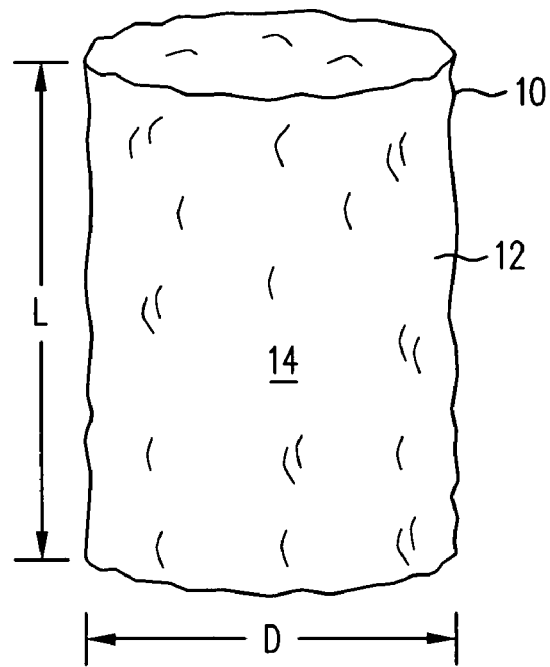
FIG. 1 is a front perspective view in enlarged format of a representative drug delivery unit produced from the compositions discussed herein which is suitable for use in accordance with the claimed methods.

As noted above, the present invention involves a unique and highly effective method for delivering therapeutic agents into the inner ear and adjacent tissue regions via the round window membrane. The "round window membrane" consists of a thin, cellular membrane structure positioned within a cavity in the middle ear known as the "round window niche". Both of these structures are illustrated and discussed in U.S. Pat. No. 5,421,818 to Arenberg et al. which is incorporated herein by reference. The round window membrane has a number of important physical features including a semi-permeable character that enables therapeutic agents (e.g. molecules) to be readily transferred across the membrane by diffusion, osmosis, active/passive transport, and the like as outlined further below. The round window membrane provides a number of unique opportunities regarding the transfer of drugs into the inner ear through the membrane. For the purposes of this invention, both the round window membrane and the round window niche shall collectively be designated herein as "middle-inner ear interface tissue structures". Likewise, the middle ear shall again be defined as the physiological air-containing tissue zone behind the tympanic membrane (e.g. the ear drum) and ahead of the inner ear. The "inner ear" basically consists of those portions of the ear contained within the otic capsule and the temporal bone which is the most dense bone tissue in the entire human body. Exemplary inner ear tissue structures of primary importance include but are not limited to the cochlea, the endolymphatic sac/duct, the vestibular labyrinth, and all of the compartments/connecting tubes which include or contain any of these components.

In order to treat various diseases and conditions associated with the inner ear, the delivery of medicines thereto is of primary importance. Representative medicines (also designated herein as "therapeutic agents") which are typically used to treat inner ear tissues in solid, liquid, semi-solid, gel, crystalline, or other forms include but are not limited to urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin), antioxidants, neurotrophins, nerve growth factors, various therapeutic peptides, and polysaccharides. Likewise, the treatment of inner ear tissues and/or fluids may involve altering the pressure, volumetric, and temperature characteristics thereof. As previously noted, a precise balance must be maintained in connection with the pressure of various fluids inside the inner ear and its associated compartments. Imbalances in inner ear fluid pressure levels can cause numerous problems, including but not limited to conditions known as endolymphatic hydrops, endolymphatic hypertension, perilymphatic hypertension, Meniere's disease, and perilymphatic hydrops.

It is a goal of this invention to provide an effective, minimally-invasive method for transferring therapeutic agents into the inner ear which is suitable for use with a wide variety of different drugs, pharmaceutical preparations, and the like as indicated below. In particular, the method described herein is site-specific relative to the round window niche and round window membrane (or other internal ear cavities as discussed below although the round window niche is of primary concern). It employs a highly-specialized drug delivery unit produced from a controlled release carrier media material combined one or more therapeutic agents. When placed in the round window niche, the therapeutic agents are released from the carrier media material using a variety of different physical mechanisms as indicated later in this section. The released therapeutic agents will then pass through the round window membrane by diffusion, osmosis, active/passive transport, and other applicable material transfer processes. The therapeutic agents will thereafter enter the inner ear (or other desired cavity) where treatment can occur. Placement of the drug delivery unit directly into the round window niche greatly facilitates this process and represents a specially-targeted delivery system which avoids premature drug delivery. It also ensures that the therapeutic agents will be transferred directly to the round window membrane and will not be inadvertently delivered to other tissue regions outside the round window niche. In this manner, drug delivery may be accomplished in a repeatable and sustained fashion without the use of complex surgical devices or drug delivery subsystems. Likewise, only a single step is needed in order to accomplish substantially "automatic", timed-release drug transfer which can occur with minimal physician monitoring and patient discomfort. For these reasons and the other reasons listed below, the claimed invention represents a substantial advance in the art of otological treatment and drug delivery.

A. Drug Delivery Units of the Present Invention

A number of different devices produced in accordance with the claimed system may be employed to achieve the goals listed above. Various embodiments of the drug delivery units (and components associated therewith) will now be discussed in detail. Thereafter, the manner in which these systems are used in a living subject will be described. It should be noted at this time that all of the dimensions, materials, components, parameters, process steps, and construction techniques listed below are provided for example purposes only, with the present invention not being limited to these items unless otherwise stated herein. In addition, the novel techniques presented below shall not be restricted to any particular theories of operation including the manner in which the drug delivery units dissolve or otherwise release therapeutic agents. These processes involve a number of highly-complex physical interactions which, while not completely understood, shall be explained to the maximum extent possible below. Finally, the term "living subject" as used herein shall encompass both humans and animals, with veterinary applications also being encompassed within the present invention.

I. The Basic Drug Delivery Unit

Figure 2:
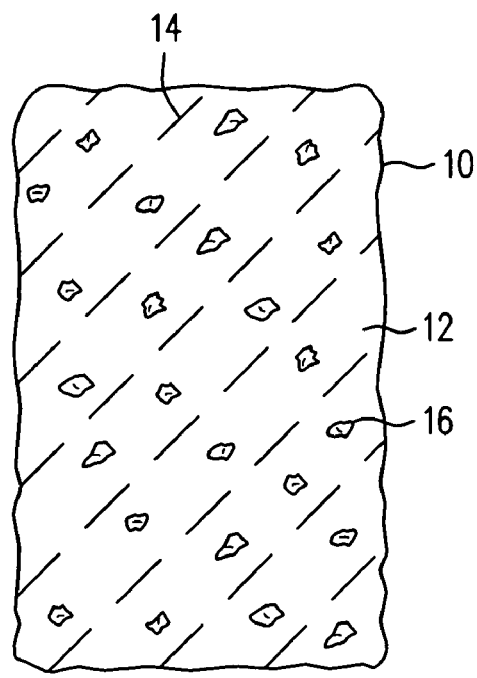
FIG. 2 is a cross-sectional view in enlarged format of the drug delivery unit of FIG. 1.

With reference to FIGS. 1-2, a structure designated herein as a "drug delivery unit" is generally illustrated at reference number 10. The drug delivery unit 10 enables controlled drug delivery into the inner ear of a human subject via the round window niche/round window membrane as previously noted. In accordance with this goal, the drug delivery unit 10 is optimally sized for partial or complete placement (e.g. "at least partial placement") within the round window niche. Again, while preferred embodiments of the invention shall be described herein with primary reference to placement of the drug delivery unit 10 in the round window niche, it may be inserted into a number of other internal cavities in the ear which will become readily apparent from the discussion provided herein. Thus, all of the information presented below regarding the drug delivery unit 10, the claimed methods, and their relationship to the round window niche shall be incorporated by reference relative to other internal ear cavities (natural or man-made) without limitation or restriction.

With continued reference to FIGS. 1-2, the drug delivery unit 10 optimally consists of a soft or semi-soft (e.g. pliable) mass 12 of a controlled release carrier media material 14. The mass 12 of carrier media material 14 is likewise combined with one or more therapeutic agents (e.g. drugs/pharmaceutical compositions in solid, liquid, gel, crystalline, or other forms) as discussed in detail below. The carrier media material 14 associated with the mass 12 is again designed to chemically release or otherwise distribute the therapeutic agents combined therewith when the drug delivery unit 10 is placed within the round window niche of a patient. Dissolution/release will occur in accordance with the unique physical environment of the round window niche (or other selected internal ear cavity) including but not limited to its pH, temperature, and moisture characteristics (as well as the chemical characteristics of the chosen carrier media material 14). If the carrier media material 14 is produced from a biodegradable compound, it will ultimately be dissolved, absorbed, and metabolized by the body after drug delivery. Non-biodegradable materials may be left in position within the niche or extracted using minimally-invasive surgical techniques as outlined below. In a preferred embodiment designed to facilitate controlled drug release, the mass 12 is optimally homogeneous and preferably of a non-porous (e.g. non-cellular) character so that the selected therapeutic agents may be delivered in a gradual manner over controlled time periods without undesired reabsorption back into the mass 12 (which might occur in connection with multi-cellular materials depending on their chemical nature). Likewise, biodegradable materials are preferred and novel in the present invention when used to produce the mass 12 since they are ultimately absorbed by the body. This avoids the need to retrieve any residual materials from the round window niche during the treatment process and thus contributes to the minimally-invasive character of the present invention. Accordingly, the placement of a biodegradable carrier media composition combined with one or more therapeutic agents specifically within the round window niche is a unique development which offers many benefits.

To accomplish the goals listed above, the carrier media material 14 is again designed to release a desired therapeutic agent over time so that it may be transferred into and through the round window membrane. The carrier media material 14 shall not be restricted to any particular chemical compositions for this purpose. The selection of any given carrier media material 14 shall be undertaken in accordance with preliminary pilot testing involving the specific inner ear conditions to be treated, the desired treatment regimen, and other related factors. Accordingly, the methods and structures claimed herein are not "carrier media-specific" with many different compositions being suitable for this purpose unless otherwise noted herein.

Exemplary and non-limiting examples of the controlled release carrier media material 14 which are suitable for use in constructing the drug delivery unit 10 will now be discussed. The following description of materials will be divided into groups for the sake of clarity and convenience.

1. Biodegradable Materials

This group of chemical compositions is preferred in the present invention and involves many different compounds which are ultimately metabolized in a safe and effective manner by the body after drug delivery is completed. From a general standpoint, the following classes of biodegradable compounds (e.g. organic polymers) may be employed in connection with the carrier media material 14: hydrophobic polyanhydrides, polyorthoesters, polyphosphazenes, polyphosphoesters/phosphoesters, and pseudopolyamino acids. All of these materials are considered to be "biodegradable", with this term being generally defined to involve a composition which will degrade or otherwise dissolve and thereafter be physiologically absorbed when placed within the human body or other living system. The applicable degradation processes associated with these materials primarily involve surface erosion, diffusion, or hydrolysis (depending on which biodegradable material is employed) which leads to gradual and controlled drug delivery. The rate of drug release (discussed further below) will depend on the particular compound selected for use which, in turn, relates to the specific side chains and side chain lengths employed in the selected polymers. Other factors which can influence the rate of drug delivery using biodegradable systems include but are not limited to the application of magnetic fields, ultrasound waves, and electric current, as well as changes in pH, temperature, and the like. The selected biodegradable materials may also be "self-oscillating" which is defined as the ability of a polymeric or other compound to swell or de-swell without any external stimuli. Finally, another important consideration in controlling drug release time involves the presence of acidic or basic excipients in combination with the chosen biodegradable polymers as discussed in, for example, Leong, K., et al., "Bioerodable polyanhydrides as drug-carrier matrices: I. Characterization, degradation, and release characteristics", *J. Biomedical Materials Research*, 19(8):941-955 (1985); and Finne, U., et al., "Timolol release from matrices of monoesters of poly (vinyl methyl ether-maleic anhydride): effects of polymer molecular weight and a basic additive", *J. Pharmaceutical Science*, 80(7):670-673 (1991).

While a number of biodegradable compositions may be employed without limitation, polyanhydride materials (which are hydrophobic in character) represent preferred materials for the purposes listed above. These compounds are generally discussed in Hollinger, J. (ed), "Biomedical Applications of Synthetic Biodegradable Polymers", CRC Press, Boca Raton, Fla. (USA) Ch. 4 by Laurencin, C., et al., pp. 59-102 (1995) Basically, in accordance with this reference, trimellitic anhydride is mixed with tyrosine to form N-trimellityrosinic acid. This material is then converted into mixed anhydrides by heating at reflux temperatures in the presence of acetic anhydride. To obtain longer polymers, aliphatic spacers are employed. As discussed in further detail below, one or more selected therapeutic agents are combined with the resulting polyanhydride product using various techniques. One of these techniques is known as "trituration" in which the drug of interest and the polymer are physically ground and mixed together in powder form. Also of interest are melt molding procedures in which the polymer is heated above its melting temperature, followed by addition of the selected drug to the molten polymer. These techniques are also applicable to the other biodegradable polymers discussed herein. Additional data concerning polyanhydride compounds for drug delivery purposes is presented in Tamada, J., et al., "The development of polyanhydrides for drug delivery applications", *Journal of Biomaterial Sciences*, Polymer Edition, 3(4):315-353 (1992). Likewise, hydrophobic biodegradable polyanhydride compounds that are particularly well suited for use as the carrier media material 14 in the mass 12 associated with the drug delivery unit 10 are commercially available from Guilford Pharmaceuticals, Inc. of Baltimore, Md. (USA).

Another biodegradable polymer which may be used as the carrier media material 14 involves polyorthoester compounds which are generally described in Merkli, A., et al., "Characterization of a new biodegradable semi-solid poly (orthoester) for drug delivery systems", *Journal of Biomaterial Sciences*, Polymer Edition, 4:505-516 (1993). Commercial sources for biodegradable polyorthoester polymers which can be employed in the drug delivery unit 10 as the carrier media material 14 include but are not limited to DSL BioMedica, Inc. of San Diego, Calif. (USA). The combination of a polyorthoester compound with a selected drug composition (e.g. gentamycin) is described in Merkli, A., et al., "Characterization of a new biodegradable semi-solid poly (orthoester) for drug delivery systems", *Journal of Biomaterial Sciences*, Polymer Edition, 4:505-516 (1993) as cited above and U.S. Pat. No. 5,461,140. To produce, for example, a mass 12 of carrier media material 14 containing a polyorthoester composition combined with gentamycin, the reactants used to fabricate the polyorthoester polymer (namely, trimethyl orthoacetate and 1,2,6,-hexanetriol) are placed in a receptacle (e.g. a round bottom flask). Under anhydrous conditions, cyclohexane is then added. The polymerization reaction is catalyzed by the addition of p-toluene sulfonic acid. This mixture is then heated under argon with vigorous stirring and, after four hours, the residual by-products (e.g. methanol) are removed. The remaining solution is then subjected to additional heating, cooling, and the addition of triethylamine to neutralize the p-toluene sulfonic acid. The liquid materials which remain at this stage are subsequently poured off, with the remaining solid polymer being dried under a vacuum. Purification of the polymer (e.g. polyorthoester) is accomplished by adding tetrahydrofuran, with the resulting mixture being precipitated using anhydrous methanol containing small amounts of triethylamine therein. The precipitated, purified polymer product is thereafter collected by filtration and dried in a vacuum oven.

In order to add the desired therapeutic agent (e.g. gentamycin in a non-limiting representative embodiment), the polyorthoester polymer product is first dissolved in anhydrous tetrahydrofuran. Gentamycin is then combined with the dissolved polymer in a 1:10 (gentamycin:polymer) weight ratio. The residual liquid solvent fraction is thereafter removed by evaporation to yield a pliable, semi-solid (e.g. soft) mass 12 which can be used as the drug delivery unit 10 in accordance with the procedures outlined below. It should be noted that the foregoing process is provided for example purposes only and shall not limit the invention in any respect. Other biodegradable and non-biodegradable polymeric carrier media materials can be combined with one or more therapeutic agents in a manner comparable to the procedure listed above which was provided for general guidance purposes.

A still further technique for producing the mass 12 of the drug delivery unit 10 using a biodegradable polymer as the carrier media material 14 involves a process known as "compression molding" as discussed in Hollinger, J. (ed), *Biomedical Applications of Synthetic Biodegradable Polymers*, CRC Press, Boca Raton, Fla. (USA) Ch. 4 by Laurencin, C., et al., p. 78 (1995) as cited above. Likewise, the mass 12 of biodegradable polymer may be formulated in a sufficiently pliable manner to permit the injection of this material (using conventional hypodermic systems) into the round window niche. The biodegradable polymer may also be formulated to produce materials known as "hydrophilic microspheres". These compositions can be employed in an injectable gel for direct introduction into a patient.

While a number of other materials (and classes thereof) can be employed as the carrier media material 14 in the present invention, the use of biodegradable polymers is preferred. These materials can be configured in many different forms, and are ultimately broken down (e.g. chemically degraded and otherwise dissolved) within the round window niche. The dissolution products are then absorbed by the body and eliminated using natural metabolic processes. The use of a biodegradable polymer as the carrier media material 14 in the drug delivery unit 10 (FIG. 1) is likewise advantageous in accordance with its ability to dissolve (in most cases) by surface erosion. Surface erosion of the drug delivery unit 10 enables more efficient, complete, and constant release of the therapeutic agent over a time period ranging from a few hours to many months. However, the exact rate of drug delivery from the mass 12 of carrier media material 14 will depend on the many factors listed above, along with the chemical composition of the biodegradable polymer, the manner in which the therapeutic agent is distributed within the polymer, and whether any basic or acidic excipients are added to the polymer as previously noted. Furthermore, drug distribution can be controlled by various chemical modifications to the selected polymer without limitation. For example, the polymer can be designed so that it also functions as a bioadhesive material, thereby facilitating proper retention in the round window niche and site-specific delivery of the desired drug. The therapeutic agent and polymer can also be selected so that they will covalently bond to each other instead of simply being mixed. This particular process will substantially influence the rate of drug delivery. Finally, multiple biodegradable polymers with differing dissolution characteristics can be combined to produce a multi-phase, composite drug delivery unit 10 with one or more "zones" that will dissolve faster than other zones. In this manner, the rate of drug release can be controlled and otherwise manipulated.

Biodegradable polymers suitable for use herein are commercially available from many sources including those listed above. A further source of these materials is Alkermes, Inc. of Cambridge, Mass. (USA). Regardless of which biodegradable polymer is selected for use in this embodiment, the combination of at least one of these materials with one or more therapeutic agents (discussed in detail below) provides many benefits. These benefits again include the ability to achieve highly-controlled drug delivery with minimal monitoring requirements and patient discomfort.

2. Hydrogels

Another class of compositions which may be used as the carrier media material 14 in the drug delivery unit 10 of FIG. 1 involves a group of materials known as "hydrogels". Hydrogels (which are primarily polymeric in character) swell in water but do not degrade. Drug release using these materials is dependent upon the amount of swelling which will vary from compound to compound, taking into consideration numerous factors including the degree of cross-linking in the hydrogel polymer of interest. Representative hydrogel compounds which may be employed to produce the drug delivery unit 10 include but are not limited to polyvinyl alcohol, polyvinyl pyrrolidone, polyethylene oxide, and polyhydroxyethyl methacrylate alone or in combination. These and other hydrogel polymers are commercially available from many sources including Polysciences, Inc. of Warrington, Pa. (USA).

To incorporate a selected therapeutic agent into a hydrogel polymer in a representative embodiment, the pH of the hydrogel is optimally reduced by about several pH units through the addition of acid materials so that premature swelling is avoided. Next, the hydrogel is heated in combination with the therapeutic agent until it is integrated into the hydrogel.

Also of interest within the hydrogel class are materials known as "microsponges" which are commercially available from Advanced Polymer Systems, Inc. of Redwood City, Calif. (USA). These compositions are produced using free-radical suspension polymerization reactions. Microsponges are manufactured from a number of polymeric precursors including but not limited to styrenics, methacrylates, and the like. Furthermore, a number of ointment materials having a hydrogel character can be employed in the drug delivery unit 10 as discussed further below.

3. Nonbiodegradable Compounds

The carrier media material 14 can also be produced from compositions classified as "nonbiodegradable compounds" which are capable of effective drug delivery in accordance with the present invention. While they will not biodegrade in the round window niche (or other internal ear cavity), they are able to accomplish drug delivery by diffusion or other related processes. Specifically, in a drug delivery unit 10 made from materials in this group (which are primarily polymeric in character), the therapeutic agents will diffuse outwardly from the unit 10 over time in accordance with the specialized cross-linked character of the nonbiodegradable polymers. The selection of any given composition within this class (as determined by preliminary pilot testing) will depend on the amount of cross-linking in the compound. The degree of cross-linking will again control drug delivery rates.

While the present invention shall not be restricted to any particular nonbiodegradable, primarily diffusion-type polymers, exemplary and preferred compositions within this class shall encompass without limitation ethylene vinyl acetate, silicone, polyethylene, polyvinyl chloride, polyurethane, and mixtures thereof. Of particular interest is the use of silicone materials which are commercially available from numerous sources including the Dow Corning Company of Midland, Mich. (USA) under the name "SILASTICS". Commercial silicone products are typically supplied as a "prepolymerized" mixture which is combined with a therapeutic agent and catalyzed to complete the production process in accordance with standard techniques discussed in, for example, Golomb, G., et al., "Controlled-Release Drug Delivery of Diphosphonates to Inhibit Bioprosthetic Heart Valve Calcification: Release Rate Modulation with Silicone Matrices via Drug Solubility and Membrane Coating", *J. Pharm. Sci.,* 76(4)271-276 (1987). However, in general, the production of a drug delivery unit 10 from one or more of the materials listed above is accomplished by levigating the drug of interest in the selected polymer. This process yields a completed drug delivery unit 10 that contains about 10-30% by weight therapeutic agent therein.

4. Soluble Compounds

A still further class of materials which may be used to produce the carrier media material 14 involves a group of products known as "soluble" compounds (which are primarily polymeric in nature). Representative compositions in this class include hydroxypropylmethyl cellulose and hydroxyethyl cellulose. These materials are capable of timed-release drug delivery primarily by diffusion as the polymeric material is broken-down by enzymes within the body. While this embodiment of the invention shall not be restricted to any particular soluble polymer sources, they may be commercially obtained from, for example, Union Carbide Chemicals and Plastics Company, Inc. of Bound Brook, N.J. (USA).

5. Miscellaneous Materials

Various sources of additional data exist concerning the materials listed above and other compounds that can be used as the carrier media material 14 in the mass 12 of the drug delivery unit 10. For example, U.S. Pat. Nos. 4,343,931 and 5,350,580 which are incorporated herein by reference discuss the following controlled-release compositions: polyesteramides, polyglycolic acid, polyvinyl alcohol, copolymers of polyethylene oxide/polylactic acid, and copolymers of glycolide/lactide. Likewise, controlled-release drug delivery products which employ "poly-L-lactic acid" compounds are discussed in (1) Goycoolea, M., et al., "Extended Middle Ear Drug Delivery", *Acta Otolaryngol.* (*Stockh.*), Suppl. 493: 119-126 (1992); and (2) Goycoolea, M., et al., "In Search of Missing Links in Otology. II. Development of an Implantable Middle Ear Drug Delivery System: Initial Studies of Sustained Ampicillin Release for the Treatment of Otitis Media", *Laryngoscope,* 101:727-732 (July 1991) which are likewise incorporated herein by reference.

In addition, a number of other "miscellaneous" compounds can be employed as the carrier media material 14 in the mass 12 of the drug delivery unit 10 (FIG. 1). These materials include patch-like structures sized for insertion within the round window niche which consist of an impermeable backing membrane, a rate-limiting center membrane, and a "basement" membrane containing a bioadhesive material (e.g. polycarbophil, polyvinyl pyrrolidone, polyvinyl alcohol, hydroxyethyl cellulose, hydroxypropylmethyl cellulose, and the like). The resulting patch products (which are substantially soluble in character) can attach to mucosa (including the interior side wall of the round window niche) for variable amounts of time up to about 1-2 hours in duration or more. Other patch structures of interest may be constructed from bilayer mucoadhesive polymers consisting of a "fast release" layer and a "sustained release" layer in order to achieve controlled drug release over a 24-hour period or longer.

The drug delivery unit 10 may also be produced from a carrier media material 14 consisting of an "ointment"-type base sold under the name "Orabase" by the Colgate-Palmolive Company of New York, N.Y. (USA) which is a bioadhesive product. It is produced from sodium carboxymethyl cellulose, polyethylene, pectin, and mineral oil. This product can remain within the body and deliver therapeutic agents for up to about 150 minutes or more in typical applications. Other ointment materials suitable for use in producing the drug delivery unit 10 include but are not limited to copolymers of polymethylvinyl ether/maleic anhydride mixed with gelatin, polyethylene, and mineral oil. A still further formula within the ointment category consists of polymethyl methacrylate mixed with water, sodium hydroxide, glycerol, and tretinoin. Likewise, other ointment formulations of interest are produced from a composition known as "Carbopol" which consists of polyacrylic acid cross-linked with divinyl glycol and is commercially available from, for example, the Thornley Company of Wilmington, Del. (USA). This material may be used as the carrier media material 14 alone or combined with additional ingredients including but not limited to hydroxypropyl cellulose and other polymeric compounds, plasticizers, and the like. Finally, another composition within this category consists of triamcinolone acetonide which is a bioadhesive-based material designed for sustained drug delivery.

Tablet-like units which employ a bioadhesive delivery system may also be used in connection with the drug delivery unit 10. Exemplary materials in this category are basically described in U.S. Pat. No. 4,226,848. This product consists of a two-layer tablet-like structure having a hydroxypropyl cellulose/"Carbopol" (see above) bioadhesive layer and a lactose-based non-adhesive backing layer. An impermeable backing membrane may also be employed within this structure for unidirectional drug delivery. Other tablet systems suitable for use in connection with the drug delivery unit 10 include those produced from chitosan/alginate derivatives.

Finally, additional compositions in the "Miscellaneous" category which may be employed as the carrier media material 14 include bioadhesive gels produced from hydroxypropyl cellulose (discussed above) and carbomer compounds, as well as hyaluronic acid and derivatives thereof.

Notwithstanding the information, materials, and formulations listed above, this invention shall not be limited to any particular chemical compositions in connection with the carrier media material 14 used in the mass 12 of the drug delivery unit 10 except as otherwise noted below. The selection of any given composition within the classes listed above will involve preliminary pilot testing taking into account many factors including the specific therapeutic agents to be used, the treatment protocol under consideration, and other factors. However, it is important to note that the carrier media material 14 should be of synthetic origin (without any animal-derived products combined therewith) in order to avoid allergic reactions, biological rejection, and other adverse effects which may be caused by animal-derived compounds (such as gelatin materials, collagen products, and the like). In this regard, the term "synthetic" as used herein shall be defined to encompass materials of a non-animal origin, with the placement of a synthetic carrier media material 14 directly in the round window niche constituting a novel development with a high safety profile. It should also be noted that the term "animal" as used herein shall also encompass humans. Thus, the word "synthetic" shall likewise exclude products of human origin. Representative synthetic carrier media materials 14 again include those listed above which are devoid of animal based compounds such as gelatin, collagen, and others. For example, exemplary synthetic carrier media materials 14 include but are not limited to hydrophobic polyanhydrides, polyphosphazenes, polyvinyl alcohol, polyvinyl pyrrolidone, ethylene vinyl acetate, silicone, and others. Also, non-cellular and non-porous carrier media materials 14 are preferred as previously noted.

Next, with reference to the cross-sectional view of FIG. 2, the mass 12 associated with the drug delivery unit 10 includes at least one therapeutic agent 16 which is combined with the carrier media material 14 as discussed above. The terms "combined", "comprises", and "comprising" as they apply to the carrier media material 14 containing the therapeutic agent 16 shall encompass many different situations. For example, these terms will involve mixtures of both materials in which the therapeutic agent 16 is dispersed randomly, uniformly, or in one or more discrete locations within the carrier media material 14. Likewise, the therapeutic agent 16 may be positioned entirely inside the carrier media material 14 or can be dispersed on the outside of the carrier media material 14 as a coating on all or part of the surface thereof. Accordingly, the present invention shall not be limited to any manner in which the therapeutic agent 16 is combined with the carrier media material 14.

In the embodiment of FIG. 2 (which is provided for example purposes only), the therapeutic agent 16 is randomly dispersed throughout the carrier media material 14 in discrete zones as illustrated. The location of the therapeutic agent 16 within the carrier media material 14 will influence the rate of drug delivery. For example, therapeutic agents 16 that are "buried" deep within the carrier media material 14 will normally take longer to be released compared with a drug delivery unit 10 having the therapeutic agents 16 located at the surface of the carrier media material 14. Thus, by modifying the location of the therapeutic agent 16 within the carrier media material 14, drug release time can be controlled as needed and desired.

Regarding the particular therapeutic agents 16 which can be employed in the drug delivery unit 10, this term shall be construed to cover a wide variety of materials including drugs, pharmaceutical preparations, and the like. A single therapeutic agent 16 or multiple therapeutic agents 16 can be employed, depending on the conditions being treated. Likewise, the therapeutic agents 16 retained on or within the drug delivery unit 10 can involve liquids, solids (e.g. powders, crystals, and the like), gels, pastes, and any other forms which are necessary as determined by routine preliminary testing. In order to treat various conditions of the inner ear (and other tissue regions), a number of medicines are important. Representative materials encompassed within the phrase "therapeutic agents" that are of primary interest include but are not limited to urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin/ampicillin), antioxidants, steroids, anesthetics, neurotrophins, nerve growth factors, therapeutic peptides, polysaccharides, artificial perilymph, iron chelators, calcium antagonists, glutamate antagonists, dopamine agonists, gamma-aminobutyric acid, interleukin converting enzyme inhibitors, calpain inhibitors, C-type natriuretic peptides, cochlear blood flow agents, prostaglandins, gene therapy agents, cytotoxic agents, osmotic drugs, antihistimines, cholinergic compounds, anti-viral drugs, and the like. Either a single therapeutic agent 16 or multiple therapeutic agents 16 in combination can be employed.

From a therapeutic standpoint, the treatment of inner ear tissues and/or fluids may involve altering the pressure, volumetric, and temperature characteristics thereof. A precise balance must be maintained in connection with the pressure of various fluids inside the inner ear and its associated compartments. Imbalances in inner ear fluid pressure levels can cause numerous problems, including but not limited to conditions known as endolymphatic hydrops, endolymphatic hypertension, perilymphatic hypertension, Meniere's disease, and perilymphatic hydrops as previously noted. Thus, the delivery of therapeutic agents to the inner ear in accordance with the site-specific method of the present invention provides many important benefits including the control of inner ear pressure levels. It should also be noted that this invention shall not be limited to any particular therapeutic agents, with the compositions listed above being provided for example purposes. Many different materials can be employed depending on numerous factors including the specific condition being treated, the overall physical state of the patient, and other related factors. Thus, the present invention shall not be considered "therapeutic agent-specific".

As previously indicated, either a single therapeutic agent 16 or multiple therapeutic agents 16 can be employed in connection with the drug delivery unit 10 as again determined by the particular needs of the patient under consideration. Likewise, a single carrier media material 14 or multiple carrier media materials 14 can be used in combination to control drug delivery in a very precise manner. If a single carrier media material 14 is employed, the resulting drug delivery unit 10 will be characterized as a "single phase" system. A drug delivery unit 10 with multiple carrier media materials 14 therein is appropriately classified as a "multi-phase" system. Both of these systems can be used with the therapeutic agents 16 listed above (and other materials) to treat a variety of conditions including but not limited to tinnitus (inner ear origin), vertigo (inner ear origin), sensorineural hearing loss, and Meniere's disease.

As previously noted, all of the various embodiments of the drug delivery unit 10 described in this section shall not be restricted to any specific numerical parameters and formulations. However, in a representative and preferred embodiment, the mass 12 associated with the drug delivery unit 10 will contain about 60-90% by weight total carrier media material 14 (whether a single media material 14 or multiple media materials 14 are employed, with the above-listed range involving the total [combined] amount of carrier media materials 14). Likewise, the mass 12 associated with the drug delivery unit 10 will optimally contain about 10-40% by weight total therapeutic agent 16 (whether a single therapeutic agent 16 or multiple agents 16 are employed, with the above-listed range involving the total [combined] amount of therapeutic agents 16). The above-listed ranges are independent of the manner in which the therapeutic agent 16 is dispersed on or within the carrier media material 14 and the type of therapeutic agent 16 under consideration.

Likewise, as needed and desired in accordance with routine preliminary investigation, a number of optional supplemental ingredients (not shown) can be employed within the mass 12 without restriction. The claimed invention shall not be restricted to any particular supplemental ingredients or mixtures thereof. Exemplary supplemental ingredients include but are not limited to plasticizers, lubricants, fillers, and the like (preferably of synthetic origin) which may be employed within the drug delivery unit 10 in selectively variable amounts. In a representative and non-limiting embodiment, the mass 12 associated with the drug delivery unit 10 will typically contain about 5-10% by weight total combined supplemental ingredients (if used), with the respective quantities of the carrier media material 14 and the therapeutic agent 16 being correspondingly reduced in a proportionate amount based on the quantity of optional supplemental ingredients being employed.

The drug delivery unit 10 illustrated in FIGS. 1-2 is configured substantially in the shape of a cylinder. However, the drug delivery unit 10 of the invention may be produced in many different forms without limitation including pellets, disks, tablets, plates, spheres, cubes, cylindrical units (FIGS. 1-2), strands, plugs, amorphous masses, portions of gel/paste materials, and the like which are sized for placement at least partially within the round window niche (or other desired internal ear cavity). The term "placement" or "placed" as used herein shall involve either partial or complete insertion of the drug delivery unit 10 into the round window niche or other internal ear cavity of interest (e.g. as much as is needed in accordance with the medical procedures under consideration.)

Regarding the size characteristics of the mass 12/drug delivery unit 10, they will differ from patient to patient depending on the age of the subject, the cavity in which the drug delivery unit 10 is to be inserted, and other factors. Prior to the treatment of a particular patient, a preliminary assessment may be undertaken in order to select the optimum size characteristics of the drug delivery unit 10 in order to achieve a maximum degree of effectiveness. Taking all of these factors into consideration, it can again be stated that the mass 12 associated with the drug delivery unit 10 should be sized for placement either entirely or partially (e.g. "at least partially") within the round window niche of a living subject or other internal ear cavity in an alternative embodiment. To accomplish this goal, a number of representative dimensions will now be provided which shall be regarded as non-limiting.

With reference to FIG. 1, the mass 12 associated with the drug delivery unit 10 will be substantially cylindrical (e.g. circular in cross-section) with a representative length "L" of about 0.5-20 mm and diameter "D" of about 0.5-4 mm. These dimensional ranges should encompass human subjects and animals of varying age, and will likewise be applicable to the round window niche and the other internal ear cavities of importance as outlined further below. The foregoing dimensions may be translated to all other shapes associated with the drug delivery unit 10 of the present invention, with any needed adjustments being made in accordance with the size characteristics of the patient being treated. Again, the exact dimensions associated with the selected drug delivery unit 10 may be varied within the ranges listed above or as otherwise needed in accordance with preliminary observation and assessment of the patients under consideration.

B. Insertion of the Drug Delivery Unit 10 in Position

Many different methods, techniques, and approaches may be used for inserting the drug delivery unit 10 into a patient provided that the unit 10 ultimately resides within the desired cavity (e.g. the round window niche). The term "resides" as used herein shall involve a situation in which the drug delivery unit 10 is located entirely or partially ("at least partially") within the round window niche, either spaced apart from the round window membrane or positioned adjacent to and against the membrane. The drug delivery unit 10 may fill the niche entirely or only partially. Furthermore, the drug delivery unit 10 may actually be larger than the niche, with only a portion of the unit 10 fitting into the niche. It shall therefore be understood that placement of the drug delivery unit 10 in the round window niche will encompass all of the variations listed above without limitation. Likewise, while the following discussion will focus on the round window niche, it shall be applicable to insertion of the drug delivery unit 10 in other internal ear cavities as further defined later in this section although it is a particularly novel development to place the drug delivery unit 10 in the round window niche as discussed herein.

Figure 3:
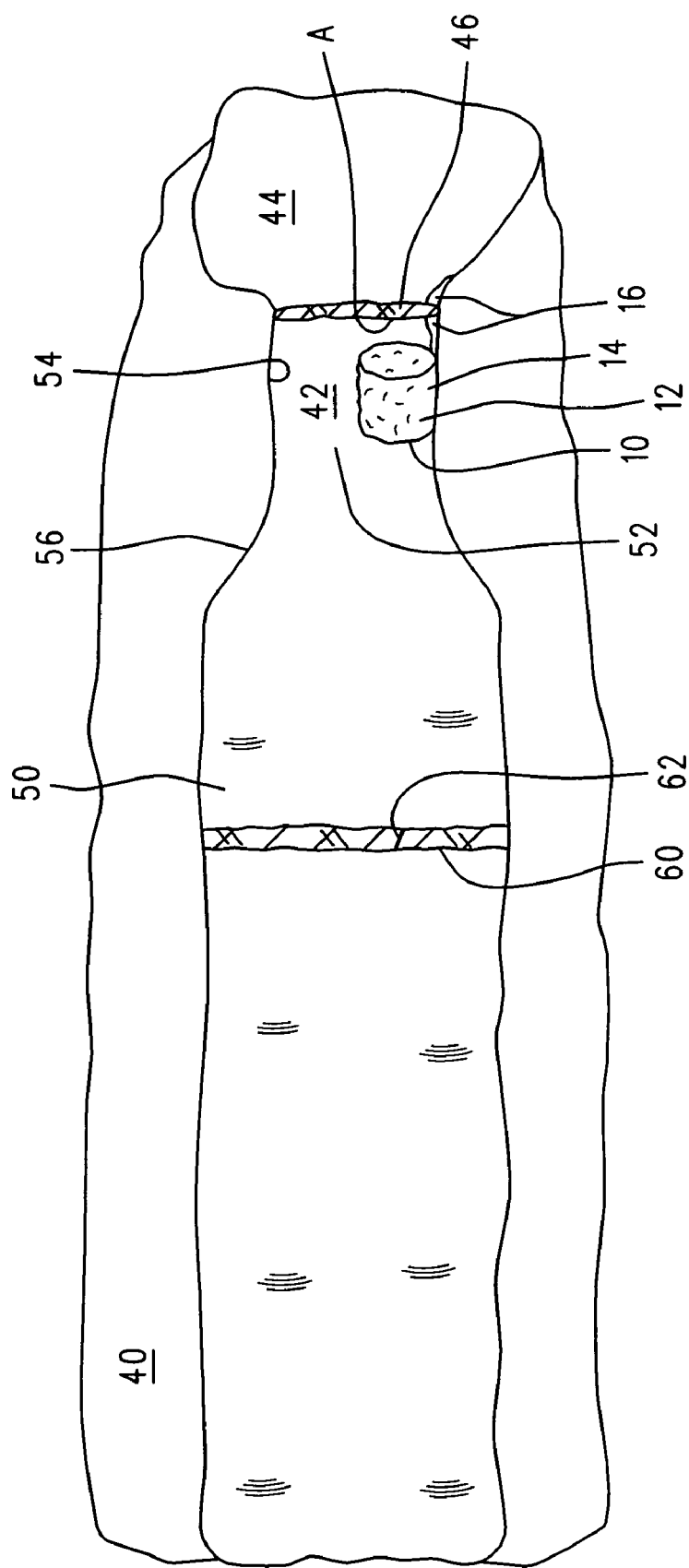
FIG. 3 is a schematic representation of the drug delivery unit of FIGS. 1-2 positioned within the round window niche of a patient adjacent to the round window membrane.
Figure 7:
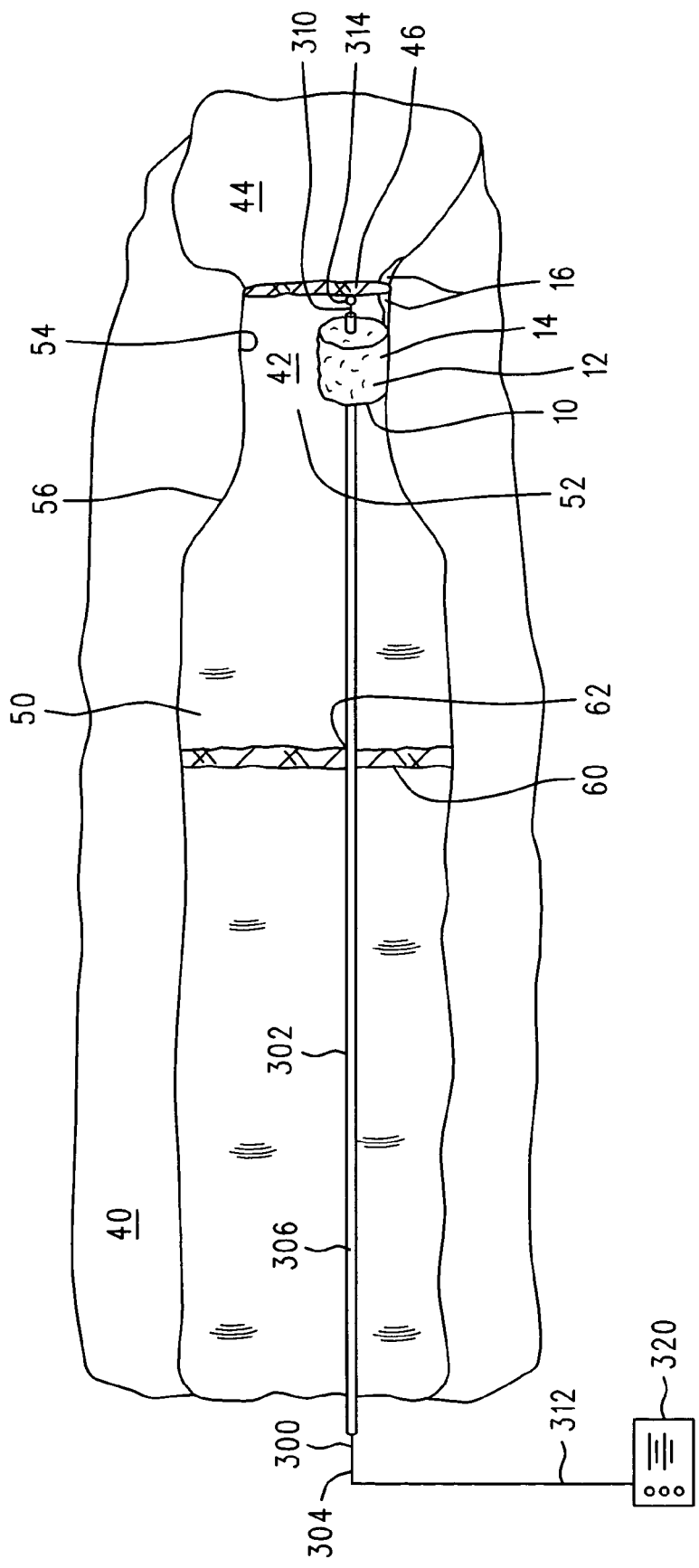
FIG. 7 is a schematic representation of the drug delivery unit of FIGS. 1-2 positioned on the conductive member of FIG. 6 which is inserted in the ear of a patient.

Many different methods may be used to insert the mass 12 associated with the drug delivery unit 10 into the round window niche as previously noted, ranging from injection into the round window niche through the tympanic membrane if an injectable polymeric material is employed to surgical procedures of a minimally-invasive nature. These surgical procedures are of primary interest and will now be discussed. All of the methods and techniques discussed below shall be applicable to the drug delivery unit 10 regardless of its shape, form, or chemical content. Furthermore, the structures of the human ear illustrated in FIGS. 3 and 7 are schematic in nature and enlarged for the sake of clarity. More detailed information concerning these structures is provided in U.S. Pat. No. 5,421,818 which is again incorporated herein by reference.

FIG. 3 is a schematic, partial cross-sectional view of the ear 40 in a human subject illustrating the drug delivery unit 10 of FIGS. 1-2 inserted therein. As shown in FIG. 3, the drug delivery unit 10 is positioned so that it is entirely located within the round window niche, generally designated in FIG. 3 at reference number 42. The inner ear is shown at reference number 44, with the specific components of the inner ear 44 (including the cochlea, the endolymphatic sac, and the endolymphatic duct being omitted for the sake of clarity and illustrated in U.S. Pat. No. 5,421,818). The round window membrane is generally designated at reference number 46, and constitutes an interface tissue structure between the middle ear 50 and the inner ear 44. The round window niche 42 basically consists of an internal cavity 52 which further includes an interior side wall 54 and a main opening 56 leading into the internal cavity 52. The drug delivery unit 10 is located in FIG. 3 at a position which is spaced apart (and outwardly) from the round window membrane 46. However, in an alternative embodiment, the drug delivery unit 10 may be placed at position "A" in FIG. 3 where it would come in direct contact with the round window membrane 46 and thereby be positioned against this structure.

Insertion of the drug delivery unit 10 in the embodiment of FIG. 3 is accomplished by passing the unit 10 (using an appropriate microsurgical instrument of conventional design) through the tympanic membrane 60 (illustrated schematically in FIG. 3). The tympanic membrane 60 preferably has an incision 62 therein that allows the drug delivery unit 10 to pass therethrough. The drug delivery unit 10 may alternatively pass beneath a tympanomeatal flap (not shown) depending on the techniques chosen by the surgeon. If an injectable carrier media material 14 is employed in connection with the drug delivery unit 10, the needle portion of the injection system (not shown) is passed through the incision 62 in the tympanic membrane 60 (or through the tympanomeatal flap) in the same manner discussed above in connection with the non-injectable drug delivery unit 10 of FIG. 1. It should likewise be noted that proper orientation and/or insertion of the drug delivery unit 10 within a patient may be accomplished through the use of a conventional operating microscope or otologic endoscope apparatus of the type disclosed in U.S. Pat. No. 5,419,312 to Arenberg et al. (incorporated herein by reference).

At this point, it shall again be emphasized that the present invention is not limited to (1) any methods for placement of the drug delivery unit 10 in position within the ear 40; and (2) any particular orientation in connection with the drug delivery unit 10 provided that it is at least partially positioned within the round window niche 42 in a preferred embodiment. Placement of the drug delivery unit 10 in the niche 42 will cause it to come in contact with at least a portion of the interior side wall 54. As a result, drug delivery is facilitated. In addition, packing materials of the type normally used for medical applications can be employed within the ear 40 to further secure the drug delivery unit 10 in its desired location. Once the drug delivery unit 10 is in position as shown in FIG. 3, it can then be used to deliver the therapeutic agent 16 of interest into the inner ear 44 via the round window membrane 46. Specifically, the drug delivery unit 10 at this stage is "allowed" to release the therapeutic agent 16 therefrom in accordance with the mechanisms discussed herein. The term "allowed" as used in connection with the release of therapeutic agents 16 from the drug delivery unit 10 shall comprise leaving the drug delivery unit 10 in the patient (e.g. the round window niche 42) until therapeutic agent delivery occurs on a partial or complete basis. This may involve a time period ranging from minutes to hours, depending on the compositions under consideration.

The released therapeutic agent 16 subsequently flows by gravity, by pump, or other comparable forces/interactions toward and into the round window membrane 46. Thereafter, the therapeutic agent 16 can travel through the round window membrane 46 and into the inner ear 44 for the treatment of tissues, fluids, fluid compartments, and tissue regions therein. Passage of the therapeutic agent 16 through the round window membrane 46 takes place in accordance with the unique permeable character of this structure as discussed in detail above and in U.S. Pat. No. 5,421,818. A number of physical processes can occur regarding passage of the therapeutic agent 16 through the round window membrane 46 including but not limited to osmosis, diffusion, active/passive transport, and the like.

The manner in which the therapeutic agent 16 is released from the drug delivery unit 10 will again depend on the particular carrier media composition 14 that is employed. Delivery of the therapeutic agent 16 is described above in connection with the multiple carrier media materials 14 which may be used in this invention. Specifically, release of the therapeutic agent 16 from the drug delivery unit 10 can occur via many different processes ranging from biodegradation if the carrier media material 14 is biodegradable to the swelling of hydrogel materials if these compounds are employed as the carrier media material 14. In addition, it may also be possible or desirable as determined by routine preliminary testing to add one or more supplemental fluid materials (e.g. water, saline solutions, and the like) into the round window niche 42 along with the drug delivery unit 10 to facilitate more rapid and uniform release of the therapeutic agent 16. Supplemental fluid delivery may be accomplished using a conventional syringe apparatus inserted in the same manner discussed above relative to the drug delivery unit 10 (e.g. via an incision 62 in the tympanic membrane 60 or through a tympanomeatal flap [not shown]). However, the present invention shall not require supplemental fluid delivery which is an optional procedure that may be used if needed or desired, with the delivered quantity of supplemental fluid being determined by routine preliminary testing. Furthermore, delivery of the supplemental fluid can be accomplished in many other ways, including transfer using the procedures, devices, and components disclosed in co-owned U.S. Pat. Nos. 5,421,818; 5,474,529, and 5,476,446 all to Arenberg et al., as well as co-owned and pending U.S. patent application Ser. No. 08/874,208 (filed on Jun. 13, 1997) and Ser. No. 09/121,460 (filed on Jul. 23, 1998) both to Arenberg et al. as cited above.

Drug delivery times and rates will vary from one carrier media composition 14 to another. Delivery times can range from minutes to many months, with the particular carrier media composition 14 of interest being selected in accordance with the desired delivery time as again determined by routine experimental testing. This testing will also take into account the effects of pH, moisture levels, and other environmental factors associated with the round window niche 42 which typically have an influence on drug release rates.

C. Additional Embodiments

Many variations of the drug delivery unit 10 and claimed drug delivery methods within the scope of the invention are possible. These variations all incorporate the novel concept described herein, namely, the placement of a controlled release, therapeutic agent-containing drug delivery unit 10 into the round window niche of a patient (or other internal ear cavity), followed by drug release from the unit 10. Thus, all of the information, data, techniques, materials, and procedures discussed above in connection with the previous embodiments are equally applicable to and incorporated by reference in this section of the present discussion.

An alternative drug delivery apparatus involves placement of the drug delivery unit 10 on the end of an elongate member of variable size, shape, and construction material so that the unit 10 can be appropriately placed within the round window niche 42. This embodiment of the invention shall not be limited to any particular construction materials, sizes, or shapes in connection with the elongate member. Many different construction materials can be employed for this purpose including but not limited to plastic compounds (e.g. polyethylene, polycarbonate, and other medically acceptable plastics), metallic compositions (e.g. stainless steel, titanium, silver alloys, and the like), or any other materials that are acceptable for medical use in the ear. The elongate member may be hollow, solid, stiff, flexible, porous, elastomeric, or a combination of these characteristics. The overall length of the elongate member may also be varied as needed, ranging from 5-150 mm as determined by routine preliminary testing. In a preferred embodiment, the elongate member will be sufficiently long to enable the treating physician to manipulate the position of the drug delivery unit 10 within the round window niche 42 of a patient from a location outside the ear (or from the middle/external ear as needed).

Figure 4:
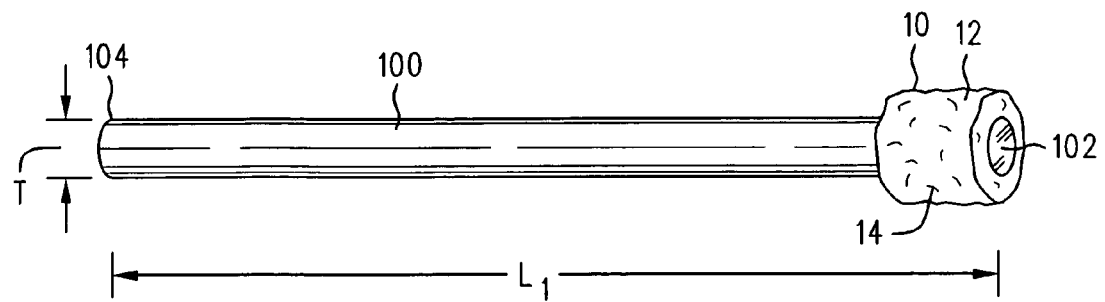
FIG. 4 is a schematic representation of the drug delivery unit of FIGS. 1-2 positioned on the end of a solid, rod-like elongate member.
Figure 5:
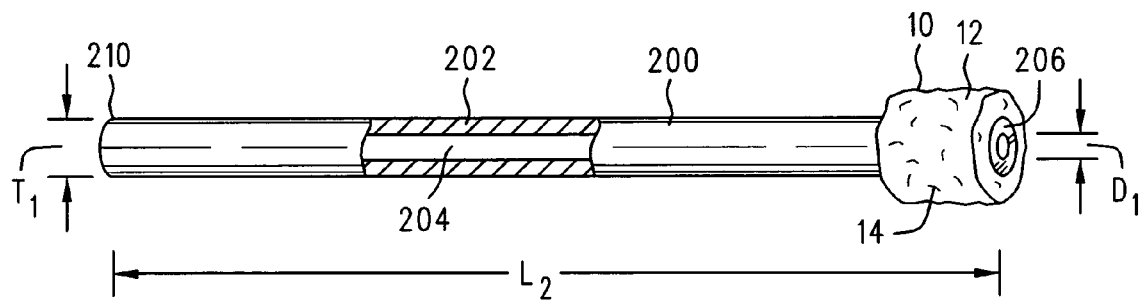
FIG. 5 is a schematic representation of the drug delivery unit of FIGS. 1-2 positioned on the end of a hollow (e.g. tubular) elongate member which is partially shown in cross-section.
Figure 6:
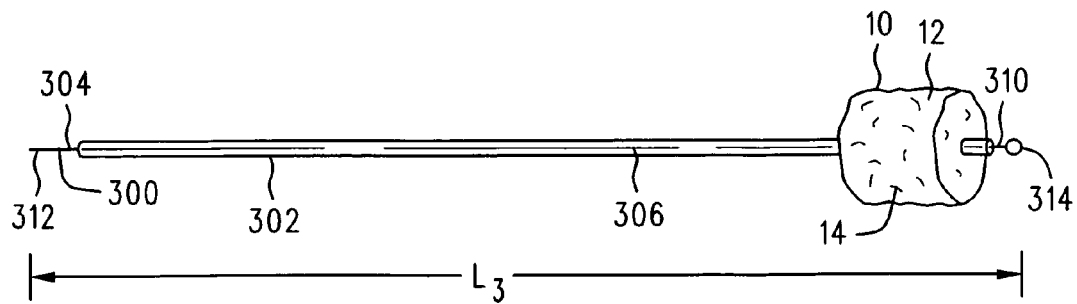
FIG. 6 is a schematic representation of the drug delivery unit of FIGS. 1-2 positioned on the end of an elongate member in the form of an electrically conductive element (e.g. a wire or the like).

FIGS. 4-6 schematically illustrate various elongate members having the drug delivery unit 10 secured thereto. Attachment of drug delivery unit 10 can be achieved using many different techniques including (1) molding of the drug delivery unit 10 onto the terminal end of the elongate member during production of the unit 10; and/or (2) adhesion of the drug delivery unit 10 to the terminal end of the elongate member using one or more medically-approved adhesive compounds including a material known as "autologous fibrin glue" as described in U.S. Pat. No. 4,874,368 to Miller et al. (which is incorporated herein by reference) or a cyanoacrylate compound. The amount and type of adhesive (as well as the extent to which the drug delivery unit 10 is molded onto the elongate member if this technique is chosen) will vary, depending on whether the drug delivery unit 10 is to remain on the elongate member during use or be detachable therefrom.

With continued reference to FIG. 4, a rod or shaft-like elongate member 100 is illustrated which is of solid construction and produced from one or more of the materials listed above (e.g. plastic). The terms "rod" or "shaft" shall encompass solid or partially solid members having a circular, square, or other cross-sectional configuration. The elongate member 100 has a proximal or first end 102 and a distal or second end 104. The overall length "$L_1$" associated with the specific elongate member 100 in a preferred embodiment is about 10-150 mm, with the thickness "T" thereof being about 0.5-2 mm. Both of these ranges shall be considered non-limiting and exemplary in nature. The first end 102 includes the drug delivery unit 10 attached thereto using at least one of the attachment methods listed above.

FIG. 5 illustrates (partially in cross-section) an alternative elongate member 200 in the form of a hollow, tubular structure having a continuous side wall 202 and a passageway 204 therethrough which is surrounded by the side wall 202. The elongate member 200 may be produced from one or more of the materials listed above including surgical-grade plastic. The elongate member 200 has a proximal or first end 206 and a distal or second end 210. The overall length "$L_2$" associated with the specific elongate member 200 in a preferred embodiment is about 5-150 mm, with the diameter or thickness "$T_1$" thereof being about 0.5-2 mm. Likewise, the diameter "$D_1$" associated with the passageway 204 is about 0.1-1 mm. Again, these ranges are provided for example purposes only and shall be considered non-limiting. The first end 206 includes the drug delivery unit 10 attached thereto using at least one of the attachment methods listed above. This embodiment is particularly useful in accordance with its ability to transfer fluid materials and the like through the passageway 204 in the elongate member 200 if needed and desired as discussed above.

Finally, FIG. 6 involves a further alternative system which employs an elongate conductive member 300 that functions as an electrical potential transmission system 302. The system 302 is designed to receive evoked or non-evoked electrical potentials from middle/inner ear tissues and transmit them out of the ear for detection and analysis. Likewise, the electrical potential transmission system 302 may be employed to deliver electrical potentials to the middle/inner ear for treatment purposes regarding a number of conditions including but not limited to tinnitus.

In a preferred embodiment, the electrical potential transmission system 302 will again consist of the elongate conductive member 300 which may involve a variety of different structures. For example, it is preferred that the elongate conductive member 300 consist of a thin wire 304 (e.g. #27 gauge) manufactured from titanium, silver, platinum, mixtures thereof, or other highly conductive materials. The wire 304 is preferably coated with an optional layer 306 of insulation material thereon. Representative insulation materials suitable for this purpose include but are not limited to heat shrinkable Teflon® (polytetrafluoroethylene) tubing of a type that is well known in the art. The wire 304 further includes a proximal or first end 310 and a distal or second end 312 as illustrated (FIG. 6). It should also be noted that the elongate conductive member 300 may involve other structures equivalent to the wire 304. For example, a substantially flat, flexible metallic strip (not shown) may be used in place of the wire 304, although the wire 304 is preferred. Regarding the wire 304 and structures equivalent thereto, it is again preferred that these components be coated with an insulating material as previously noted (e.g. see layer 306), although the use of an insulating composition is not required in all cases.

As shown in FIG. 6, the first end 310 of the elongate conductive member 300/wire 304 has the drug delivery unit 10 attached thereto (e.g. positioned on the layer 306 of insulation material in the embodiment of FIG. 6) using one of the methods listed above. The first end 310 of the wire 304 may further include an optional conductive spherical member 314 secured thereto (e.g. integrally formed thereon). The spherical member 314 is preferably positioned ahead of and outwardly from the drug delivery unit 10. The spherical member 314 is optimally manufactured from the same material used to construct the wire 304 as outlined above. Use of the spherical member 314 facilitates direct contact between the wire 304 and the ear tissues of concern (e.g. the round window membrane or other desired structures). In an alternative embodiment (not shown), the first end 310 of the wire 304 may include a rounded club or hook-like portion thereon as shown in U.S. Pat. No. 5,421,818 or a loop, spoon, flat, or mushroom-shaped structure instead of the spherical member 314. Thus, the spherical member 314 may be substituted with a number of comparable structures in a non-limiting manner. While the elongate conductive member 300 (e.g. wire 304) is primarily discussed herein as a means to receive electrical potentials, it may again be possible to use the member 300 to apply electrical potentials to ear tissues of interest in order to (1) measure responsive stimuli therefrom; (2) treat the tissues using therapeutic electrical pulses; and/or (3) implement iontophoresis procedures. Thus, the elongate conductive member 300/wire 304 of the claimed invention shall not be exclusively limited to the receipt of electrical potentials. In addition, the term "electrical potential" as used herein shall be broadly construed to encompass any type of electrical signal, current, voltage, or impulse regardless of form, magnitude, or origin.

The second end 312 of the wire 304 associated with the elongate conductive member 300 preferably extends outwardly form the ear of the patient. The second end 312 (if desired) is readily connected to an external monitoring apparatus 320 (FIG. 7) of conventional design which collects and characterizes resting or evoked electrical potentials received from the inner ear. Further information concerning the monitoring apparatus 320 is presented below.

As previously stated, the elongate conductive member 300 is particularly designed to receive electrical potentials which originate within selected inner ear tissues. This capability is especially useful in connection with a process known as "ECoG" which is an abbreviation for "electrocochleography". Electrocochleography is a known technique for measuring electrical potentials from the inner ear which basically involves measurement of the whole nerve-cochlear action potential (hereinafter "AP"). Alternatively, ECoG can be employed to indirectly measure hair cell electrical activity. ECoG can also be used to measure the summating potential (hereinafter "SP") within the inner ear in response to externally generated clicks, tone bursts, and/or pips. The SP is basically a D.C. distortion potential which can indicate the amount of distortion in the cochlear duct associated with endolymphatic hydrops or other changes in the inner ear. The relative amount of distortion may be expressed either as an SP/AP ratio (in response to externally-generated clicks, etc.), or as an absolute measurement in response to specific, externally-generated tone bursts and the like. Cochlear microphonics can also be measured as well as otoacoustic emissions (hereinafter "OAE") in order to assess hair cell function or dysfunction. Finally, endocochlear potentials can be measured using the components described herein if selected portions of the elongate conductive member 300/wire 304 are operatively positioned within the cochlea rather than outside of the cochlea. Further information on ECoG is presented in Portmann, M., "Electrophysiological correlates of endolymphatic hypertension and endolymphatic hydrops: an overview of electrocochleography (ECoG)", Proceedings of the Third International Symposium and Workshops on the Surgery of the Inner Ear, Snowmass, Colo. (USA) Jul. 29-Aug. 4, 1990 as reported in *Inner Ear Surgery*, edited by I. Kaufman Arenberg, Kugler Publications, Amsterdam/N.Y., pp. 241-247 (1991) and in U.S. Pat. No. 5,421,818 which are both incorporated herein by reference. The elongate conductive member 300/wire 304 may also be employed in connection with iontophoresis techniques which, as previously noted, involve a modification of the permeability characteristics of the round window membrane 46 using electrical signals.

Thus, as stated above, the elongate conductive member 300 is especially useful in the implementation of conventional ECoG procedures. Resting or evoked electrical potentials received by the wire 304 through direct contact of the first end 310 (e.g. the spherical member 314) with selected ear tissues (particularly the round window membrane 46) are routed through the wire 304 to the second end 312. The second end 312 of the wire 304 is operatively connected (using conventional electrical connecting clips and the like) to the monitoring apparatus 320 as indicated above and shown schematically in FIG. 7. An exemplary monitoring apparatus 320 suitable for use herein consists of commercially available ECoG detection systems sold under the names "Viking II™" and "Spirit™" by Nicolet, Inc. of Madison, Wis. (USA). However, a variety of different commercial systems may be employed to receive and quantify electrical potentials delivered by the wire 304, including but not limited to computer-monitored voltage amplifier/analog-to-digital converter units known in the art. In a preferred embodiment designed for use with ECoG systems, the wire 304 is sufficiently long to enable the second end 312 to terminate at a position outside of the patient's ear 40. In this manner, attachment of the second end 312 of the wire 304 to the monitoring apparatus 320 is greatly facilitated. Dimensional information regarding the wire 304 associated with the elongate conductive member 300 will be provided below.

Use of the wire 304 as shown in FIG. 6 provides a number of important benefits including those related to ECoG and iontophoresis techniques as previously discussed. Likewise, the operation of this particular system in cooperation with the drug delivery unit 10 will enable electrophysiological measurements to be correlated with the effects of drug materials delivered by the unit 10. While the elongate conductive member 300 is an optional element in the present invention, it may nonetheless be used (if desired in accordance with preliminary pilot studies) on any or all of the various embodiments outlined herein.

Regarding the overall length "$L_3$" associated with the elongate conductive member 300/wire 304 illustrated in FIG. 6, an optimum and non-limiting range will be about 100-150 mm which is sufficient to accomplish the goals listed above. It should also be noted that all of the elongate members which may be used in connection with the drug delivery unit 10 (including elongate members 100, 200, 300) may remain attached to the drug delivery unit 10 during release of the therapeutic agent 16 as previously discussed or can be removed by appropriate physical manipulation of the elongate member so that the drug delivery unit 10 detaches therefrom. Again, the detachability of the drug delivery unit 10 will depend upon the manner in which it is secured to the elongate member as previously discussed.

Regarding insertion into the ear 40 of the elongate members 100, 200, 300 (and any structures equivalent thereto which may be used in connection with the drug delivery unit 10), a number of different methods can be employed without limitation. While FIG. 7 specifically illustrates the elongate conductive member 300 having the drug delivery unit 10 attached thereto, it shall be understood that the information provided below regarding insertion methods is equally applicable to the other elongate members associated with this invention including elongate members 100, 200. With continued reference to FIG. 7, the first end 310 of the wire 304 associated with the elongate conductive member 300 is optimally passed through the incision 62 in the tympanic membrane 60 (or beneath a surgically formed tympanomeatal flap [not shown]). The first end 310 of the wire 304 again includes the drug delivery unit 10 operatively attached thereto. The second end 312 of the wire 304 will preferably be positioned outside the patient's ear 40 where it is attached to the equipment mentioned above (including the monitoring apparatus 320). The first end 310 of the wire 304 and attached drug delivery unit 10 will ultimately reside within the round window niche 42, with the spherical member 314 being in direct physical contact with the round window membrane 46 for ECoG monitoring and the other purposes mentioned above. In addition, the first end 310 of the wire 304 (e.g. the spherical member 314) can instead be placed in contact with tissue structures adjacent the round window membrane 46 which shall be deemed equivalent thereto including but not limited to the mucosa/bone of the round window niche 42 and others. The drug delivery unit 10 may be positioned on the first end 310 of the wire 304 (e.g. on the layer 306 of insulation material in the embodiment of FIGS. 6 and 7) at a location which allows the wire 304 and attached spherical member 314 to extend outwardly from the unit 10 as illustrated (FIG. 7). Alternatively, the first end 310 of the wire 304 and spherical member 314 may be entirely embedded within the drug delivery unit 10, with the exposure thereof taking place during drug delivery when the drug delivery unit 10 erodes or otherwise dissolves (assuming that a biodegradable or dissolvable carrier media material 14 is employed). In this regard, placement of the wire 304 (including the spherical member 314) against the round window membrane 46 may take place before, after, or during drug delivery, with all of these alternatives being considered equivalent. Removal of the elongate conductive member 300 (or the other elongate members 100, 200 discussed herein) may be achieved by reversing the process described above. Furthermore, for reference purposes, it should be noted that the combined drug delivery unit 10 and elongate member 100, 200, or 300 shall be characterized herein as a "drug delivery apparatus".

In a still further embodiment, the drug delivery unit 10 may be placed on or otherwise used in connection with the medicine delivery devices disclosed in co-owned U.S. Pat. Nos. 5,421,818; 5,474,529, and 5,476,446 all to Arenberg et al., as well as co-owned and pending U.S. patent application Ser. Nos. 08/874,208 (filed on Jun. 13, 1997) and 09/121,460 (filed on Jul. 23, 1998) also to Arenberg et al. as cited above.

The claimed drug delivery systems and methods provide numerous benefits and capabilities including: (1) the repeatable and sustained delivery of therapeutic agents into the inner ear through the round window membrane [or other middle-inner ear interface structures]; (2) the delivery of many different therapeutic agents (e.g. pharmaceutical preparations) to the inner ear in a safe and direct manner; (3) the accomplishment of effective drug delivery without overly invasive surgical procedures; and (4) the use of a simplified method to deliver therapeutic agents into the inner ear of a patient without complex medical procedures, monitoring, and patient discomfort. For these reasons and the other factors listed above, the present invention represents a substantial advance in the art of otological treatment and diagnosis.

As a final point of information, a preferred embodiment of the invention involves insertion of the drug delivery unit 10 (and all variants thereof) inside the round window niche of a living subject (which is a novel development of primary interest). However, the drug delivery unit 10 can likewise be placed at least partially within any cavity or opening (natural or man-made) in the external auditory canal, middle ear, and/or inner ear (with all of these cavities/openings collectively being designated herein as "internal cavities"). Representative internal cavities, structures, or regions within the ear which may receive the devices listed above include but are not limited to the oval window, operculum, endolymphatic duct, the hypotympanum, and/or any bony crevice, overhang, or other region which will assist in anchoring the present invention in position. The term "internal cavity" shall also be defined to encompass any zones or regions between adjacent tissue structures (e.g. muscles, tendons, ligaments, and the like.) All of the embodiments described herein may be used with these and other internal cavities in the same manner previously discussed in connection with the round window niche (although the round window niche is of primary interest and again constitutes a particularly novel development which offers many benefits). Accordingly, the information provided herein regarding insertion of the drug delivery unit 10 within the round window niche shall be incorporated by reference relative to other internal ear cavities without limitation. Nonetheless, it is of primary interest and novelty to specifically insert the controlled-release drug delivery unit 10 within the round window niche (compared with other ear regions). This novelty resides in the unique ability of the released drug materials to come in direct contract with the round window membrane which permits the rapid diffusion thereof into the inner ear. The round window niche and its special proximity to the round window membrane therefore offers a number of opportunities and efficiencies which cannot be obtained by insertion of the drug delivery unit 10 into other ear regions. Thus, by inserting the drug delivery unit 10 specifically into the round window niche, site-specific transfer of the therapeutic agents to the round window membrane is ensured. This process, in combination with the controlled release capabilities of the drug delivery unit 10, provides a system which produces highly-effective results and avoids inadvertent drug delivery to other non-inner ear regions.

Having herein described preferred embodiments of the invention, it is anticipated that suitable modifications may be made thereto by individuals skilled in the art which nonetheless remain within the scope of the invention. For example, the invention shall not be limited with respect to the construction materials being employed, the compositions used to produce the drug delivery unit 10, and the physiological environment in which the invention is used unless otherwise indicated. In systems involving the use of an elongate member, more than one elongate member can be employed with any given drug delivery unit. Also, more than one drug delivery unit can be used in all of the systems and embodiments disclosed herein (including those which involve one or more elongate members). In this regard, the invention shall only be construed in accordance with the following claims:

The invention that is claimed is:

1. A method for delivering a therapeutic agent into the inner ear of a living subject, said method comprising:
   providing a drug delivery unit comprising a carrier material and a therapeutic agent combined therewith, wherein said carrier material provides for controlled release of the therapeutic agent from said drug delivery unit over time, and further wherein
   said drug delivery unit is configured as a pellet, disk, tablet, plate, sphere, cube, cylindrical unit, or strand, and
   said drug delivery unit is shaped and sized for partial or complete insertion into the round window niche of the subject; and
   inserting said drug delivery unit directly into the round window niche of the subject such that said unit is positioned either partially or completely within the round window niche, wherein the therapeutic agent is released from the drug delivery unit, contacts the round window membrane and passes into the inner ear.

2. The method of claim 1, wherein said therapeutic agent is released over a period of 24 hours.

3. The method of claim 1, wherein said therapeutic agent is released over a period of hours.

4. The method of claim 1, wherein said therapeutic agent is released over a period of months.

5. The method of claim 1, wherein said carrier material comprises a polymer.

6. The method of claim 1, wherein said therapeutic agent is selected from the group consisting of urea, mannitol, sorbitol, glycerol, lidocaine, xylocaine, epinephrine, immunoglobulins, sodium chloride, steroids, heparin, hyaluronidase, aminoglycoside antibiotics, antioxidants, neurotrophins, nerve growth factors, various therapeutic peptides, and polysaccharides.

7. The method of claim 6, wherein the therapeutic agent is an aminoglycoside antibiotic.

8. The method of claim 7, wherein the aminoglycoside antibiotic is gentamycin.

9. The method of claim 1, wherein said drug delivery unit is shaped and sized for complete insertion into the round window niche of the subject.

10. The method of claim 1, wherein said drug delivery unit is shaped and sized for partial or complete insertion as a detached unit into the round window niche of the subject.

11. The method of claim 10, wherein said drug delivery unit is shaped and sized for complete insertion as a detached unit into the round window niche of the subject.

12. The method of claim 10, wherein said drug delivery unit is positioned at a location which is spaced apart from the round window membrane.

13. The method of claim 1, wherein said drug delivery unit has a volume of between 0.1 mm$^3$ and 250 mm$^3$.

14. The method of claim 1, wherein said carrier material is capable of delivering the therapeutic agent to the inner ear in nanogram to microgram quantities.

15. The method of claim 1, wherein said therapeutic agent is present in a quantity of between about 10 wt % and 40 wt % of the total weight of the drug delivery unit.

16. The method of claim 1, wherein said carrier material comprises a polyanhydride material.

17. The method of claim 1, wherein said carrier material comprises a polyorthoester material.

18. The method of claim 1, wherein said carrier material comprises hydroxypropylmethyl cellulose.

19. The method of claim 1, wherein said carrier material comprises hydroxyethyl cellulose.

20. The method of claim 1, wherein said carrier material comprises hydrophilic microspheres.

21. The method of claim 1, wherein said carrier material comprises a bioadhesive material.

22. The method of claim 1, wherein said drug delivery unit is a multiphased composite drug delivery unit.

23. The method of claim 1, wherein said release of said therapeutic agent is achieved by osmosis, diffusion, active/passive transport, or a combination thereof.

24. The method of claim 1, wherein the carrier material is biodegradable.

25. The method of claim 1, wherein the carrier material is synthetic.

26. The method of claim 1, wherein release of the therapeutic agent from the drug delivery unit is without inadvertent delivery to other tissue regions outside the round window niche.

* * * * *